US006165461A

United States Patent [19]
Cobb et al.

[11] Patent Number: 6,165,461
[45] Date of Patent: Dec. 26, 2000

[54] TAO PROTEIN KINASES AND METHODS OF USE THEREFOR

[75] Inventors: Melanie Cobb; Michele Hutchison; Zhu Chen; Kevin Berman, all of Dallas, Tex.

[73] Assignee: Board of Regents, University of Texas System, Austin, Tex.

[21] Appl. No.: 09/060,410

[22] Filed: Apr. 14, 1998

[51] Int. Cl.$^7$ .............................. A61K 38/51; C12N 9/12
[52] U.S. Cl. .......................................... 424/94.5; 435/194
[58] Field of Search .............................. 435/194; 424/94.5

[56] References Cited

FOREIGN PATENT DOCUMENTS

WO 99/02699   1/1999   WIPO .

OTHER PUBLICATIONS

Boulton et al., "An Insulin–Stimulated Protein Kinase Similar to Yeast Kinases Involved in Cell Cycle Control," *Science* 249:64–67, 1990.
Burbelo et al., "A Conserved Binding Motif Defines Numerous Candidate Target Proteins for Both Cdc42 and Rac GTPases," *J. Biol. Chem. 270*: 29071–29074, 1995.
Courhesne et al., "A Putative Protein Kinase Overcomes Pheromone–Induced Arrest of Cell Cycling in S. cerevisiae," *Cell 58*: 1107–1119, 1989.
Elion et al., "FUS3 Encodes a cdc2+/CDC28–Related Kinase Required for the Transition from Mitosis into Conjugation," *Cell 60*: 649–664, 1990.
Hunter and Plowman, "The protein kinases of budding yeast: six score and more," *Trends in Biochem. Sci.* 22:18–22, 1997.
Leberer et al., "The protein kinase homologue Ste20p is required to the link yeast pheromone response G–protein βγ submits to downstream signalling components," *The EMBO Journal 11*:4815–4824, 1992.
Ramer and Davis, "A dominant truncation allele identifies a gene, STE20, that encodes a putative kinase necessary for mating in *Saccharomyces cerevisiae*," *Proc. Natl. Acad. Sci. USA 90*:452–456, 1993.
Rhodes et al., "STE11 is a protein kinase required for cell–type–specific transcription and signal transduction in yeast," *Genes and Development 4*: 1862–1874, 1990.
Robinson et al., "Contributions of the Mitogen–activated Protein (MAP) Kinase Backbone and Phosphorylation Loop to MEK Specificity," *The Journal of Biological Chemistry 271*(47): 29734–29739, 1996.
Su et al., "NIK is a new Ste20–related kinase that binds NCK and MEKK1 and activates the SAPK/JNK cascade via a conserved regulatory domain," *The EMBO Journal 16*(6): 1279–1290, 1997.
Teague et al., "Nucleotide sequence of the yeast regulatory gene STE7 predicts a protein homologous to protein kinases," *Proc. Natl. Acad. Sci. USA 83*: 7371–7375, 1986.
Wu et al., "Molecular Characterization of Ste20p, a Potential Mitogen–activated Protein or Extracelluar Signal–regulated Kinase Kinase (MEK) Kinase Kinase from *Saccharonmyces cerevisiae*," *Journal of Biological Chemistry 270*(27): 15984–15992, 1995.
Allen et al., "PAK2 Mutation in Nonsyndromic X–Linked Mental Retardation," *Nature Genetics 20*:25–30, 1998.
Creasy and Chernoff, "Cloning and Characterization of a Member of the MST Subfamily of Ste20–Like Kinases," *Gene 167*:303–306, 1995.
Database EMBL Accession No. AA234623, Mar. 6, 1997.
Database EMBL Accession No. AF068864, Sep. 23, 1998.
Hutchinson et al., "Isolation of TAO1, a Protein Kinase That Activates MEKs in Stress–Activated Protein Kinase Cascades," *J. Biol. Chem.* 273(44):28625–28632, 1998.
Marra et al., genban–est111 database, Accession No. g1541866, Sep. 1996.

*Primary Examiner*—Rebecca E. Prouty
*Assistant Examiner*—Maryam Monshipouri
*Attorney, Agent, or Firm*—Seed IP Law Group

[57] ABSTRACT

Compositions and methods are provided for potentiating the activity of the mitogen-activated protein kinase p38. In particular the mitogen-activated protein kinase kinase MEK6, and variants thereof that stimulate phosphorylation of p38 are provided. Such compounds may be used, for example, for therapy of diseases associated with the p38 cascade and to identify antibodies and other agents that inhibit or activate signal transduction via p38.

8 Claims, 19 Drawing Sheets

```
   1 TCTGCAGTATGGTAGATTATTATTTATGCATTTATGCCAGTGTGGCTTCATTCATACAGATGAACCAAGCTTTGGGATAGCAGTATAAAATTAGAATCAGACAGCTGACTGCTC
 115 AGCAGGATGCCATCAACTAACAGAGCAGGCAGTCTAAAGGACCCTGAAATCGCAGAGCTCTTCTTCAAAGAAGATCCGGAAAAACTCTTCACAGATCTCAGAGAAATCGGCCAT
        M  P  S  T  N  R  A  G  S  L  K  D  P  E  I  A  E  L  F  F  K  E  D  P  E  K  L  F  T  D  L  R  E  I  G  H    36

229 GGGAGCTTTGGAGCAGTTTATTTTGCACGAGATGTGCGTACTAATGAAGTGGTGGCCATCAACAAAATGTCTTATAGTGGAAAGCAGTCTACTGAGAAATGGCAGGATATTATT
        G  S  F  G  A  V  Y  F  A  R  D  V  R  T  N  E  V  V  A  I  K  K  M  S  Y  S  G  K  Q  S  T  E  K  W  Q  D  I  I   74

343 AAGGAAGTCAAGTTTCTACAAACAATAAAACATCCCAACAGTATAGAATACAAAGGCTGCTATTTACGTGAACACACAGCATGGCTTGTAATGGAATATTGTTTAGGATCTGCT
        K  E  V  K  F  L  Q  R  I  K  H  P  N  S  I  E  Y  K  G  C  Y  L  R  E  H  T  A  W  L  V  M  E  Y  C  L  G  S  A  112

457 TCGGATTTACTAGAAGTTCATAAAAAGCCATTACAAGAAGTGGAAATAGCAGCAATTACACATGGTGCTCTCCAGGGATTAGCTTATTTACATTCTCATACCATGATCCATAGA
        S  D  L  L  E  V  H  K  K  P  L  Q  E  V  E  I  A  A  I  T  H  G  A  L  Q  G  L  A  Y  L  H  S  H  T  M  I  H  R  150

571 GATATCAAAGCAGGAAATATCCTTCTGACAGAACCAGGCCAAGTGAAACTTGCTGACTTTGGATCTGCTTCCATGGCCTCCCCTGCCAATTCTTTTGTGGGAACACCATATTGG
        D  I  K  A  G  N  I  L  L  T  E  P  G  Q  V  K  L  A  D  F  G  S  A  S  M  A  S  P  A  N  S  F  V  G  T  P  Y  W  188

685 ATGGCCCCACAAGTAATTTTAGCCATGGATGAAGGACAATATGATGGCAAAGTTGATGTATGGTCTCTTGGAATAACATGTATTGAATTAGCCGAGAGGAAGCCTCCTTTATTT
        M  A  P  E  V  I  L  A  M  D  E  G  Q  Y  D  G  K  V  D  V  W  S  L  G  I  T  C  I  E  L  A  E  R  K  P  P  L  F  226

799 AATATGAATGCAATGAGTGCCTTATATCACATAGCCCAAAATGAATCCCCTACACTACAGTCTAATGAATGGTCTGATTATTTTCGAAACTTTGTAGATTCTTGCCTCCAGAAA
        N  M  N  A  M  S  A  L  Y  H  I  A  Q  N  E  S  P  T  L  Q  S  N  E  W  S  D  Y  F  R  N  F  V  D  S  C  L  Q  K  264

913 ATCCCTCAAGATCGCCCTACATCAGAGGAACTTTTAAAGCACATGTTTGTTCTTCGAGAGCGCCCTGAAACAGTGTTAATAGATCTTATTCAAAGGACAAAGGATGCAGTAAGA
        I  P  Q  D  R  P  T  S  E  E  L  L  K  H  M  F  V  L  R  E  R  P  E  T  V  L  I  D  L  I  Q  R  T  K  D  A  V  R  302

1027 GAGCTGGACAATCTACAATATCGAAAGATGAAGAAACTCCTTTTCCAGGAGGCACATAATGGACCAGCAGTAGAAGCACAGGAAGAAGAGGAGGAGCAAGATCATGGTGGTGGC
        E  L  D  N  L  Q  Y  R  K  M  K  K  L  L  F  Q  E  A  H  N  G  P  A  V  E  A  Q  E  E  E  E  E  Q  D  H  G  G  G  340

1141 CGGACAGGAACAGTAAATAGTGTTGGAAGCAATCAGTCTATCCCCAGTATGTCTATCAGTGCCAGTAGCCAAAGCAGCAGTGTTAATAGTCTTCCAGATGCATCGGATGACAAG
        R  T  G  T  V  N  S  V  G  S  N  Q  S  I  P  S  M  S  I  S  A  S  S  Q  S  S  S  V  N  S  L  P  D  A  S  D  D  K  378

1255 AGTGAGCTAGACATGATGGAGGGAGACCATACAGTGATGTCTAACAGTTCTGTCATCCACTTAAAACCTGAGGAGGAAAATTACCAAGAAGAAGGAGATCCTAGAACAAGAGCA
        S  E  L  D  M  M  E  G  D  H  T  V  M  S  N  S  S  V  I  H  L  K  P  E  E  E  N  Y  Q  E  E  G  D  P  R  T  R  A  416

1368 TCAGCTCCACAGTCTCCACCTCAAGTGTCTCGTCACAAATCACATTATCGTAATAGAGAACACTTTGCAACTATACGAACAGCATCACTGGTTACAAGACAGATGCAAGAACAT
        S  A  P  Q  S  P  P  Q  V  S  R  H  K  S  H  Y  R  N  R  E  H  F  A  T  I  R  T  A  S  L  V  T  R  Q  M  Q  E  H  454

1483 GAGCAGGACTCTGAACTTAGAGAACAGATGTCTGGTTATAAGCGGATGAGGCGACAGCATCAGAAGCAGCTGATGACTCTGGAAAATAAACTGAAGGCAGAAATGGACGAACAT
        E  Q  D  S  E  L  R  E  Q  M  S  G  Y  K  R  M  R  R  Q  H  Q  K  Q  L  M  T  L  E  N  K  L  K  A  E  M  D  E  H  492

1597 CGGCTCACATTAGACAAAGATCTTGAAACTCAGCGCAACAATTTCGCTGCAGAAATGGAGAAACTTATTAAGAAACACCAAGCTTCTATGGAAAAAGAGGCTAAAGTGATGGCC
        R  L  T  L  D  K  D  L  E  T  Q  R  N  N  F  A  A  E  M  E  K  L  I  K  K  H  Q  A  S  M  E  K  E  A  K  V  M  A  530
```

*Fig. 1A*

1711 AACGAGGAGAAAAAATTCCAACAACACATTCAGGCTCAACAGAAGAAAGAACTGAATAGCTTTTTGGAGTCTCAAAAAAGAGAATATAAACTTCGAAAAGAGCAGCTTAAGGAG
     N E E K K F Q Q H I Q A Q Q K K E L N S F L E S Q K R E Y K L R K E Q L K E   568

1825 GAGCTGAATGAAAACCAGAGCACACCTAAAAAAGAAAAGCAGGAATGGCTTTCAAAGCAGAAGGAGAATATTCAACATTTTCAGGCAGAAGAAGAAGCTAATCTTCTTCGACGT
     E L N E N Q S T P K K E K Q E W L S K Q K E N I Q H F Q A E E E A N L L R R   606

1939 CAAAGGCAGTATCTAGAGCTAGAATGTCGTCGCTTCAAAAGAAGAATGTTACTTGGTCGGCATAACTTGGAACAGGACCTTGTCAGGGAGGAGTTAAACAAAAGGCAGACTCAG
     Q R Q Y L E L E C R R F K R R M L L G R H N L E Q D L V R E E L N K R Q T Q   644

2053 AAGGACTTAGAACATGCAATGTTACTGCGACAGCATGAATCCATGCAAGAACTGGAGTTTCGCCACCTCAACACTATTCAGAAGATGCGCTGTGAGTTGATCAGACTGCAACAT
     K D L E H A M L L R Q H E S M Q E L E F R H L N T I Q K M R C E L I R L Q H   682

2167 CAAACTGAGCTTACTAACCAGCTGGAATACAATAAGAGAAGGGAACGGGAACTAAGACGGAAACATGTCATGGAAGTTCGACAGCAGCCTAAGAGTTTGAACTCTAAAGAACTC
     Q T E L T N Q L E Y N K R R E R E L R R K H V M E V R Q Q P K S L K S K E L   720

2281 CAAATAAAAAAGCAGTTTCAGGATACCTGCAAAATTCAAACCAGACAGTACAAAGCATTAAGGAATCACCTACTGGAGACTACACCAAAGAGTGAGCACAAAGCTGTTCTGAAA
     Q I K K Q F Q D T C K I Q T R Q Y K A L R N H L L E T T P K S E H K A V L K   758

2395 AGACTCAAGGAGGAACAGACTCGGAAGTTAGCCATCTTGGCTGAGCAGTATGATCATAGCATTAATGAAATGCTCTCCACACAAGCTCTGCGTTTGGATGAAGCACAGGAAGCA
     R L K E E Q T R K L A I L A E Q Y D H S I N E M L S T Q A L R L D E A Q E A   796

2509 GAATGCCAGGTTTTGAAGATGCAGCTACAGCAGGAACTGGAGCTGTTGAATGCATATCAGAGCAAAATCAAGATGCAGGCTGAGGCCCAACATGATCGAGAGCTTCGAGAGCTG
     E C Q V L K M Q L Q Q E L E L L N A Y Q S K I K M Q A E A Q H D R E L R E L   834

2623 GAACAAAGGGTCTCCCTTCGGAGAGCACTCTTAGAACAGAAGATTGAAGAAGAGATGTTGGCTTTGCAGAATGAACGCACAGAACGAATACGTAGCCTGCTCGAGCGCCAGGCC
     E Q R V S L R R A L L E Q K I E E E M L A L Q N E R T E R I R S L L E R Q A   872

2737 AGAGAAATTGAAGCTTTTGACTCTGAAAGCATGAGATTAGGTTTTAGTAACATGGTCCTTTCTAATCTCTCCCCTGAGGCATTCAGCCACAGCTACCCAGGAGCTTCTAGCTGG
     R E I E A F D S E S M R L G F S N M V L S N L S P E A F S H S Y P G A S S W   910

2851 TCTCACAATCCTACTGGGGGTTCAGGACCTCACTGGGGTCATCCCATGGGTGGCACACCACAAGCTTGGGGTCATCCGATGCAAGGCGGACCCCAACCATGGGGTCACCCCTCA
     S H N P T G G S G P H W G H P M G G T P Q A W G H P M Q G G P Q P W G H P S   948

2965 GGGGCCAATGCAAGGGGTACCTCGAGGTAGCAGTATAGGAGTCCGCAATAGCCCCCAGGCTCTGAGGCGGACAGCTTCTGGGGGACGGACGGAACAGGGCATGAGCAGAAGCACG
     G P M Q G V P R G S S I G V R N S P Q A L R R T A S G G R T E Q G M S R S T   986

3079 AGTGTCACTTCACAAATATCCAATGGGTCACACATGTCTTACACATAATAATTGAAAGTGGCAATTCCGCTGGAGCTGTCTGCCAAAAGAAACTGCCTACAGACATCAGCACAG
     S V T S Q I S N G S H M S Y T * *                                             1001

3193 CAGCCTCCTCACTTGGGTACTACCGGGTGGAAGCTGTGCATATGGTATATTTTATTCGTCTTTGTAAAGCGTTATGTTTTGTGTTTACTAATTGGGATGTCATAGTATTTGGCT

*Fig. 1B*

```
                    I                                  II                    III
TAO1   MPSTNRAGSLKDPEIAELFFKEDPEKLFTDLREIGHSFGAVYFARDVRTNEVAIKKMSYSGKQSTEKW--QDIIKEV  77
TAO2   MPAGGRAGSLKDPDVAELFFKDDPEKLFSDLREIGHSFGAVYFARDVRNSEVAIKKMSYSGKQSNEKW--QDIIKEV  77
ceTAO  -MAPAVLQKPGVIKDPSIAALFSNKDPEQDLREIGHSFGAVYFAYDKKNEQTVAIKKMNFSGKQAVEKW--NDILKEV  76
STE20  REERERRKKQLYAKLNEICSDGDPSTKYANLVKIGQGASGGVYTAYEIGTNVSVAIKQMNLE-KQPKKELINEILVMK 670

IV                        V                               VI
TAO1   KFLQRIKHPNSIEYKGCYIREHTAWLVMEYCLGSASDLLEVHKKPLQEVEIAAITHGALQGLAYLHSHTMIHRDIKAGN 156
TAO2   RFLQKLRHPNTIQYRGCYIREHTAWLVMEYCLGSASEFLEVHKKPLQEVEIAAVTHGALQGLAYLHSNMIHRDVKAGN 156
ceTAO  SFINTVVHPHIVDYKACFLKDTTCWLVMEYCIGSAADIVDVLRKGMREVEIAAICSQTLDALRYLHSLKRIHRDIKAGN 155
STE20  G---SKHPNIVNFIDSYVLKGDLWVIMEYMEGFSLTDV-VTHCILTEGQIGAVCRETLSGLEFLHSKGVLHRDIKSDN 744

VII                              VIII                   IX
TAO1   ILLTEPGQVKLADFGSAS----MASPANSFVGTPYWMAPEVILAMDEGQYDGKVDVWSLGITCIELAERKPPLFNMNA 230
TAO2   ILLSEPGLVKLGDFGSAS----IMAPANSFVGTPYWMAPEVILAMDEGQYDGKVDVWSLGITCIELADRKPPLFNMNA 230
ceTAO  ILLSDHAIVKLADFGSAS----LVDPAQTFIGTPFFMAPEVILAMDEGHYTDRADIWSLGITCIELAERRPPLFSMNA 229
STE20  ILLSMEGDIKLTDFGFCAQINELNLKRTTMVGTPYWMAPEVVSRKE---YGPKVDIWSLGIMIEMIEGEPPYLNETP 819

X                                                   XI
TAO1   MSALYHIAQNESPTLQSNEWMSDYFRN------FVDSCLQKIPQDRPTSE 273
TAO2   MSALYHIAQNESPALQSGHWSEYFRN------FVDSCLQKIPQDRPTSE 273
ceTAO  MSALYHIAQNDPPTLSPIDTSEQPEWMSLEFVQFIDKCLRKPAEERMSAE 279
STE20  LRALYLIATNGTPKLKEPENLSS---SLKK--FLDWCLCVEPEDRASAT 863
```

Fig. 2

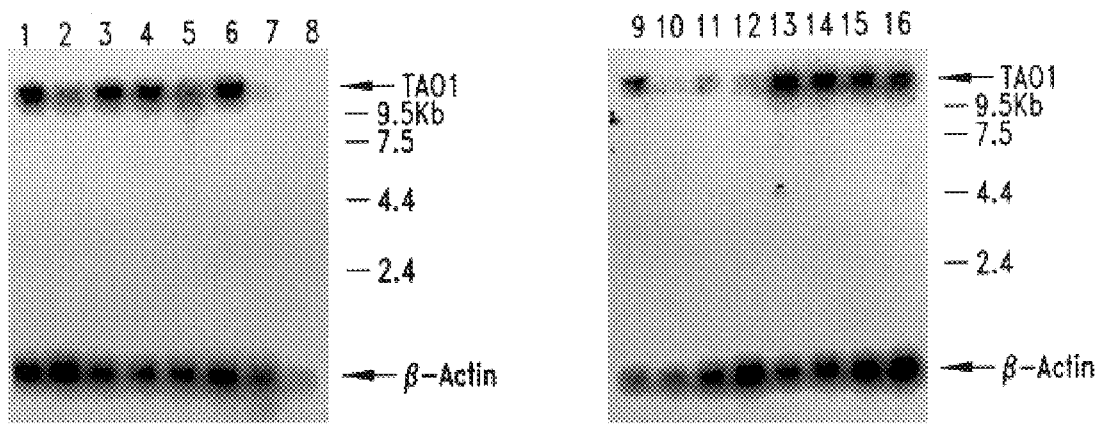
Fig. 4A　　　Fig. 4B
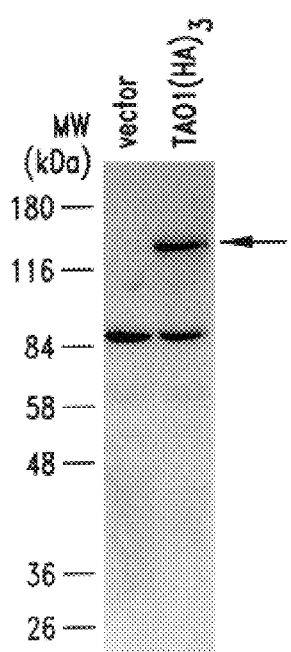 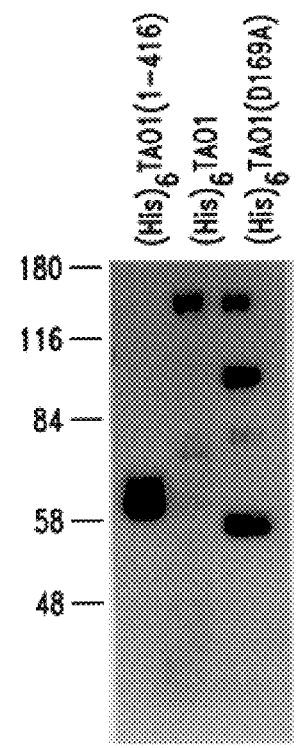 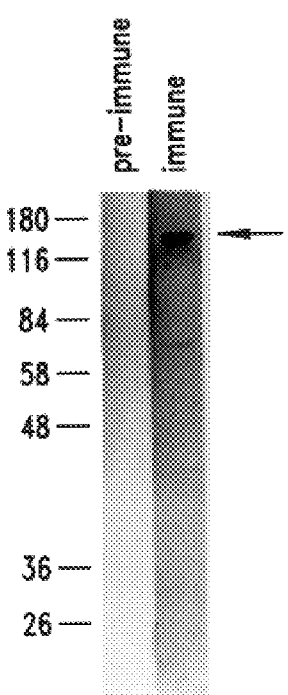
Fig. 5A　　　Fig. 5B　　　Fig. 5C

```
Query:  2341  AGGAATCACCTACTGGAGACTACACCAAAGAGTGAGCACAAAGCTGTTCTGAAAAGACTC  2400
              | ||  ||||||    ||||    |||  ||||||||| |||||||||||  |   |  ||  |  |||
Sbjct:    12  ACGANTCACCAGTTGGAAGTTACTCCAAAGAATGAGCACAAAACAATCTTAAAGACACTG   71

Query:  2401  AAGGAGGAACAGACTCGGAAGTTAGCCATCTTGGCTGAGCAGTATGATCATAGCATTAAT  2460
              || || ||  ||||||   | |||   | ||||||  |  |||  |||||||||||||| || || || |||
Sbjct:    72  AAAGATGAGCAGACAAGAAAAACTTGCCATTTNGGCAGAGCAGTATGAACAGAGTATAAAT  131

Query:  2461  GAAATGCTCTCCACACAAGCTCTGCGTTTGGATGAAGCACAGGAAGCAGAATGCCAGGTT  2520
              ||||||  |   ||  ||  ||   |  |   |||||| || || ||||||||||||||||||||
Sbjct:   132  GAAATGATGGCCTCTCANGCGTTACGGCTAGATGAGGCTCAAGAAGCAGAATGCCAGGCC  191

Query:  2521  TTGAAGATGCAGCTACAGCAGGAACTGGAGCTGTTGAATGCATATCAGAGCAAAATCAAG  2580
              ||||  |  ||||||   ||||||||||    ||||||||| |  || || |||||||||||||||||
Sbjct:   192  TTGAGGCTACAGCTCCAGCAGGAAATGGAGCTGCTCAACGCCTACCAGAGCAAAATCAAG  251

Query:  2581  ATGCAGGCTGAGGCCCAACATGATCGAGAGCTTCGAGAGCTGGAACAAAGGGTCTCCCTT  2640
              |||||  |  ||||||  ||||||||| || |||||  |   |||| || || || || || ||
Sbjct:   252  ATGCAAACAGAGGCACAACATGAACGTGAGCTCCAGAAGCTAGAGCAGAGAGTGTCTCTG  311

Query:  2641  CGGAGAGCACTCTTAGAACAGAAGATTGAAGAAGAGATGTTGGCTTTGCAGAATGAACGC  2700
              || ||||||||  |  ||  |||||||||||||||||  ||| ||    ||   ||||||  ||||||
Sbjct:   312  CGCAGAGCACACCTTGAGCAGAAGATTGAAGAGGAGCTGGCTGCCCTTCAGAAGGAACGC  371

Query:  2701  ACAGAACGAATACGTAGCCTGCTCGAGCGCCAGGCCAGAGAAATTGAAGCTTTT        2754
              |  || ||||| ||||  | ||  || | ||| |   ||||  ||||| |   |||
Sbjct:   372  AGCGAGAGAATAAAGAACCTATTGGAAAGGCAAGAGCGAGAGATTGGAAACTTT         425
```

Fig. 12

```
Query:  964 GAACAAACATGTGCTTTAAAAGTTCCTCTGATGTAGGGCGATCTTGAGGGATTTTCTGGA 905
             ||||||   |||  ||||  |||||  ||||||| ||  |  ||||| |||||||||| |
Sbjct:   79 GAACAAAGTCATGCCTTAATAGTTCTGCTGATGTTGGCCTTTCCTGAGGTATTTTCTGCA 138

Query:  904 GGCAAGAATCTACAAAGTTTCGAAAATAATCAGACCATTCATTAGACTGTAGTGTAGGGG 845
             |||  ||||  ||||||   | |||   | ||   |||||||||||||||||  || ||||
Sbjct:  139 AGCAGTAATCAACAAATCTCCTAAAGGAGTCTGTCCATTCATTAGACTGTAACGTTGGGG 198

Query:  844 ATTCATTTTGGGCTATGTGATATAAGGCACTCATTGCATTCATATTAAATAAAGGAGGCT 785
             | ||||| ||||| |||||||||||||||||||||||||||||| || |  || ||||
Sbjct:  199 AGTCATTCTGGGCAATGTGATATAAGGCACTCATTGCATTCATGTTGAAAAGGGGCGGCT 258

Query:  784 TCCTCTCGGCTAATTCAATACATGTTATTCCAAGAGACCATACATCAACTTTGCCATCAT 725
             |||  || || |||||||||||||| ||  || ||||| |||||| ||||||| ||||||
Sbjct:  259 TCCGTTCCGCCAATTCAATACAAGTGATGCCAAGTGACCAAATATCAACTTTCCCATCAT 318

Query:  724 ATTGTCCTTCATCCATGGCTAAAATTACTTCTGGGGCCATCCAATATGGTGTTCCCACAA 665
             | |||||||||||||| |||||| || || ||||||| |||||| | |||| ||||| |
Sbjct:  319 ACTGTCCTTCATCCATAGCTAAGATCACCTCTGGAGCCATCCAGTAAGGTGTGCCCACGA 378

Query:  664 AAGAATTGGCAGGG 651
             | ||  ||||| ||
Sbjct:  379 AGGAGTTGGCCAGG 392
```

*Fig. 13*

```
Query:  2792  ACCATGTTACTAAAACCTAATCTCATGCTTTCAGAGTCAAAAGCTTCAATTTCTCTGGCC  2733
              ||||  || | |||  || | |||| | |||  ||   ||||||||| |||||| ||||     |
Sbjct:    90  ACCAAATTCCCAAATCCCATTCTGAGGCTCTCCATGTCAAAAGTTTCAATCTCTCGCTCT   149

Query:  2732  TGGCGCTCGAGCAGGCTACGTATTCGTTCTGTGCGTTCATTCTGCAAAGCCAACATCTCT  2673
              || |  ||| |||| |    |||||  |||||| ||||||||| | ||   || || |||
Sbjct:   150  TGCCTTTCCAATAGGTTCTTTATTCTCTCGCTGCGTTCCTTCTGAAGGGCAGCCAGCTCC   209

Query:  2672  TCTTCAATCTTCTGTTCTAAGAGTGCTCTCCGAAGGGAGACCCTTTGTTCCAGCTCTCGA  2613
              ||||||||||||| || | |||  ||| || || || || || ||  || ||||   |
Sbjct:   210  TCTTCAATCTTCTGCTCAAGGTGTGGTCTGCGCAGAGACACTCTCTGCTCTAGCTTCTGG   269

Query:  2612  AGCTCTCGATCATGTTGGGCCTCAGCCTGCATCTTGATTTTGCTCTGATATGCATTCAAC  2553
              |||||  || ||||||| |||| |  | ||||||||| | |||| || || || || | |
Sbjct:   270  AGCTCACGTTCATGTTGTGCCTCTGTTNGNATCTTGATTTGGNTCTGGTAGGCGTTGAGC   329

Query:  2552  AGCTCCAGTTCCTGCTGTAGCTGCATCTTCAAAACCTGGCATTCTGCTTCCTGTGCTTCA  2493
              |||||||  |||||||| | |||| || |  | ||||  ||||||||||||||  ||   ||
Sbjct:   330  AGCTCCATTTCCTGCTGGAGCTGTAGCCTCAAGGCCTGGCATTCTGCTTCTTGAGCCTCA   389

Query:  2492  TCCAAACGCAGAGCTTGTGTGGAGAGCATTTCATTAATGCTATGATCATACTGCTCAGCC  2433
              || | ||| |||||| | |  |  ||||||||| || || || ||||||||||| |||
Sbjct:   390  TCTAGCCGTAACGCTTGAGAGGCCATCATTTCATTTATACTCTGTTCATACTGCTCTGCC   449

Query:  2432  AAGATGGCTA  2423
              || |||||| |
Sbjct:   450  AAAATGGCAA   459
```

*Fig. 14*

```
Query:  2248  CAGCAGCCTAAGAGTTTGAAGTCTAAAGAACTCCAAATAAAAAAGCAGTTTCAGGATACC  2307
              ||  |||||  || |  || ||| |  |   ||| | |||||| ||||| ||||||||||  ||
Sbjct:     3  CAACAGCAGAAAAACTTAAAGGCCATGGAAATGCAAATTAAAAAACAGTTTCAGGACACT    62

Query:  2308  TGCAAAATTCAAACCAGACAGTACAAAGCATTAAGGAATCACCTACTGGAGACTACACCA  2367
              ||||||  |  || ||||||||||||||||||  | ||||||||||  ||| ||  |||  |||
Sbjct:    63  TGCAAAGTACAGACCAAACAGTATAAAGCACTCAAGAATCACCAGTTGGAAGTTACTCCA   122

Query:  2368  AAGAGTGAGCACAAAGCTGTTCTGAAAAGACTCAAGGAGGAACAGACTCGGAAGTTAGCC  2427
              |||| ||||||||||  |  |  |  |||||  || ||  ||  |||||| |||  |  |||
Sbjct:   123  AAGAATGAGCACAAAACAATCTTAAAGACACTGAAAGATGAGCAGACAAGAAAACTTGCC   182

Query:  2428  ATCTTGGCTG  2437
              || ||||| |
Sbjct:   183  ATTTTGGCAG   192
```

*Fig. 15A*

```
Query:  2437  GAGCAGTATGATCATAGCATTAATGAAATGCTCTCCACACAAGCTCTGCGTTTGGATGAA  2496
              ||||||||||  || || || |||||||| | || | ||||| | || | |||||
Sbjct:   193  GAGCAGTATGAACAGAGTATAAATGAAATGATGGCCTCTCAAGCGTTACGGCTAGATGAG   252

Query:  2497  GCACA  2501
              || ||
Sbjct:   253  GCTCA   257
```

*Fig. 15B*

```
Query:  2087  ATGAATCCATGCAAGAACTGGAGTTTCGCCACCTCAACACTATTCAGAAGATGCGCTGTG  2146
              | || |||   | ||| || ||||   | || || ||||  | ||||||| | |||   |
Sbjct:    31  ACGAGTCCCCCCGAGAGCTAGAGTACAGGCAGCTGCACACGTTACAGAAGCTACGCATGG   90

Query:  2147  AGTTGATCAGACTGCAACATCAAACTGAGCTTACTAACCAGCTGGAATACAATAAGAGAA  2206
              |  ||||| |  | ||  || || || || ||    ||||||||||||||| ||||||||||||||||
Sbjct:    91  ATCTGATCCGTTTACAGCACCAGACGGAACTGGAAAACCAGCTGGAGTACAATAAGAGGC   150

Query:  2207  GGGAACGGGAACTAAGACGGAAACATGTCATGGAAGTTCGACAGCAGCCTAAGAGTTTGA  2266
              | ||| | |||||    | || |||||||||||||| |||| || |||||| ||  ||| |
Sbjct:   151  GAGAAAGAGAACTGCACAGAAAGCATGTCATGGAACTTCGGCAACAGCCAAAAAACTTAA   210

Query:  2267  AGTCTAAAGAACTCCAAATAAAAAAGCAGTTTCAGGATA  2305
              || | | ||| | ||| | |||||| ||||| ||||||| |
Sbjct:   211  AGGCCATGGAANTGCAATTTAAAAAACAGTTCCAGGAAA   249
```

Fig. 16

```
Query:  3228  GTGCATATGGTATATTTTATTCGTCTTTGTAAAGCGTTATGTTTTGTGTTTACTAATTGG  3287
              |||||||||||||||| |||| | |||||||||||| |||||||||||||||||||||||
Sbjct:    31  GTGCATATGGTATATTTNATTCATTTTTGTAAAGCGTTCTGTTTTGTGTTTACTAATTGG  90

Query:  3288  GATGTCATAGTATTTGGCTGCCGGG  3312
              ||||||||||| |||||||||||||
Sbjct:    91  GATGTCATAGTACTTGGCTGCCGGG  115
```

*Fig. 17A*

```
Query:  3200  CTCACTTGGGTACTACCGGGTGGAAGCTGTGCATATGGTATATTTT  3245
              ||||||||||||||| ||||||||||| | ||   ||| ||| ||
Sbjct:     1  CTCACTTGGGTACTACAGTGTGGAAGCTGAGTGCATATGGTATATT  46
```

*Fig. 17B*

```
Query:  739  GATGTATGGTCTCTTGGAATAACATGTATTGAATTAGCCGAGAGGAAGCCTCCTTTATTT  798
             ||| | |||||  | || || |||||| ||  | ||||| |     || || || ||
Sbjct:   14  GATATTTGGTCATTGGGTATCACGTGTATAGAGCTGGCCGAACGTCGTCCACCATTGTTC  73

Query:  799  AATATGAATGCAATGAGTGCCTTATATCACATAGCCCAAAATGAATCCCCTACACT  854
             |  |||||||||||| |||| | || || || |||||||| | || || || ||
Sbjct:   74  AGTATGAATGCAATGTCTGCCCTCTACCATATTGCTCAAAATGATCCTCCAACTCT  129
```

*Fig. 18*

```
Query:  526  CTCCAGGGATTAGCTTATTTACATTCTCATACCATGATCCATAGAGATATCAAAGCAGGA  585
             ||  |  ||  |  ||||| | || ||   |  || |||||| |||||||||||| |
Sbjct:  449  CTGAAAGGCCTGGATTATCTGCACTCAGAGCGCAAGATCCACCGAGATATCAAAGCTGCC  508

Query:  586  AATATCCTTCTGACAGAACCAGGCCAAGTGAAACTTGCTGACTTTGGATCTGCTTCCA   643
             ||  | ||  ||| ||  | ||  |||||| | || |||||| ||   ||| ||
Sbjct:  509  AACGTGCTGCTCTCGGAGCAGGGTGATGTGAAGATGGCAGACTTCGGTGTGGCTGGCA   566
```

*Fig. 19A*

```
Query:  187  GATCCGGAAAAACTCTTCACAGATCTCAGAGAAATCGGCCATGGGAGCTTTGGAGCAGTT  246
             || || || |||||||||| | ||   || ||| | ||   |||||| ||
Sbjct:  119  GACCCAGAGGAACTCTTCACCAAGCTTGACCGCATTGGCAAAGGCTCATTTGGGGAGGTG  178

Query:  247  TATTTTGCACGAGATGTGCGTACTAATGAAGTGGTGGCCATCAAGAAAAT   296
             ||   |   ||   | || || ||||||||||||||||||||||| ||
Sbjct:  179  TACAAGGGGATCGACAACCACACCAAGGAAGTGGTGGCCATCAAGATCAT   228
```

*Fig. 19B*

```
Query:  866  TCATTAGACTGTAGTGTAGGGGATTCATTTTGGGCTATGTGATATAAGGCACTCATTGCA  807
             |||  |  ||| ||    ||   ||||   |||||| |||| || || ||| || |
Sbjct:  100  TCAGGATTCTGGAGCTCTGGAGTTCCATTAGTGGCTATCAGATACAATGCCCTGAGTGGA  159

Query:  806  TTCATATTAAATAAAGGAGGCTTCCTCTCGGCTAATTCAATACATGTTATTCCAAGAGAC  747
             ||  |||||    |||| ||   |  | ||  | | ||||||      ||||||||||||
Sbjct:  160  TTTTCATTAAGGTAAGGGGGTTCACCTTCCACCATTTCAATTGCCATAATTCCAAGAGAC  219

Query:  786  CATACATCAACTTT  733
             || | |||||||||
Sbjct:  220  CAGATATCAACTTT  233
```

*Fig. 20*

TAO PROTEIN KINASES AND METHODS OF USE THEREFOR

STATEMENT OF GOVERNMENT INTEREST

The Government owns certain rights in the present invention pursuant to NIH Grant GM53032.

TECHNICAL FIELD

The present invention relates generally to compositions and methods for modulating the activity of the MAP/ERK kinase MEK3 and/or other MEK family members. The invention is more particularly related to TAO proteins, and variants thereof that stimulate phosphorylation and activation of MEK substrates, such as MEK3. The invention is further related to the use of such proteins, for example, to activate a stress-responsive MAP kinase pathway in an organism and to identify antibodies and other agents that inhibit or activate signal transduction via such a pathway.

BACKGROUND OF THE INVENTION

MAP kinase pathways are conserved signal transduction pathways that activate transcription factors, translation factors and other target molecules in response to a variety of extracellular signals. Each pathway contains a MAP kinase module, consisting of a MAP kinase or ERK, a MAP/ERK kinase (MEK), and a MEK kinase (MEKK). In higher eucaryotes, activation of MAP kinase pathways has been correlated with cellular events such as proliferation, oncogenesis, development and differentiation. Accordingly, the ability to regulate signal transduction via these pathways could lead to the development of treatments and preventive therapies for human diseases associated with MAP kinase pathways, such as inflammatory diseases, autoimmune diseases and cancer.

Several MAP kinase pathways have been found in *S. cerevisiae* (Hunter and Plowman, *Trends in Biochem. Sci.* 22:18–22, 1997), and parallel mammalian pathways have been identified based upon sequences of mammalian ERKs and yeast MAP kinases, KSS1 and FUS3 (Boulton et al., *Science* 249:64–67, 1990; Courchesne et al., *Cell* 58:1107–1119, 1989; Elion et al., *Cell* 60:649–664, 1990). The best delineated yeast MAP kinase pathway, activated by mating pheromones, is controlled by a receptor-G protein system, includes a Cdc42 small G protein, and requires at least three protein kinases, Ste20p (Leberer et al., *EMBO J.* 11:4815–4828, 1992; Ramer et al., *Proc. Natl. Acad. Sci. USA* 90:452–456, 1993), Ste11p (Rhodes et al., *Genes Dev.* 4:1862–1874, 1990), and Ste7p (Teague et al., *Proc. Natl. Acad. Sci. USA* 83:7371–7375, 1986), upstream of the MAP kinase Fus3p (Elion et al., *Cell* 60:649–664, 1990).

Ste20p was isolated from *S. cerevisiae* as a gene whose product functions downstream of the βγ subunits of a heterotrimeric G protein but upstream of enzymes in the MAP kinase module (MEKK, MEK, ERK) of the pheromone response pathway (Leberer et al., *EMBO J.* 11:4815–4828, 1992; Ramer et al., *Proc. Natl. Acad. Sci. USA* 90:452–456, 1993). Ste11p, the MEKK, may be one of the Ste20p substrates (Wu et al., *J. Biol. Chem.* 270:15984–15992, 1990); thus, Ste20p-like enzymes may activate MEKKs in mammalian MAP kinase pathways. Ste20p, like its best studied mammalian counterparts, the p21-activated protein kinases (PAKs), is thought to be regulated by binding to Cdc42 through a conserved Cdc42/Rac interactive binding region, or CRIB domain (Burbelo et al., *J. Biol. Chem.* 270:29071–29074, 1995).

Mammalian relatives of Ste20p are diverse and include the PAK subfamily (PAK1,2,3) and the mixed lineage kinase (MLK) subfamily, including the dual leucine zipper kinase (DLK), germinal center kinase (GCK), and the Nck-interacting kinase, NIK. In the past year, newly identified Ste20p-related kinases include members of the MLK subfamily, SOK-1, Krs-1 and -2, and MUK. MUK was isolated in a screen for MEKK isoforms, but in fact shows more identity to MLK. In transfected cells several of these enzymes, as first shown with GCK, increase the activity of the stress-responsive kinases, particularly SAPK/JNK. In the case of NIK and GCK, they may work by binding to MEKK (Su et al., *EMBO J.* 16:1279–1290, 1997). However, several of these Ste20p-related enzymes also have MEKK activity. For example, DLK phosphorylates and potently activates MEKs that lie in the stress-responsive cascades.

Further characterization of members of these pathways, and the identification of additional members, is critical for understanding the signal transduction pathways involved and for developing methods for activating or inactivating MEKs and MAP kinase pathways in vivo. Accordingly, there is a need in the art for improved methods for modulating the activity of members of MAP kinase pathways, and for treating diseases associated with such pathways. The present invention fulfills these needs and further provides other related advantages.

SUMMARY OF THE INVENTION

Briefly stated, the present invention provides compositions and methods for modulating the activity of MAP/ERK kinases such as MEK3, and stress-responsive MAP kinase pathways. Within certain aspects, the present invention provides TAO polypeptides. Within one such aspect, the polypeptide may comprise an amino acid sequence provided in SEQ ID NO:2 or SEQ ID NO:4, or a variant thereof in which the ability to phosphorylate MEK3 is not substantially diminished. In certain embodiments, such a polypeptide may comprise a sequence that differs from a sequence recited in SEQ ID NO:2 or SEQ ID NO:4 only in conservative substitutions and/or modifications at no more than 10% of the amino acid residues. In certain other embodiments, the polypeptide may be a constitutively active variant.

Within other aspects, the present invention provides polypeptides comprising an amino acid sequence provided in SEQ ID NO:2 or SEQ ID NO:4 modified at no more than 10% of the amino acid residues, such that the polypeptide is rendered constitutively inactive.

Within further aspects, the present invention provides polypeptides capable of phosphorylating MEK3, wherein the polypeptide does not detectably phosphorylate MEK1 or MEK2.

The present invention further provides, within other aspects, isolated polynucleotides encoding polypeptides as described above. Isolated polynucleotides comprising one or more sequences recited in any one of SEQ ID NOs:5–16, or a variant thereof, wherein the polynucleotide encodes a polypeptide capable of phosphorylating MEK3, are also provided. Polypeptides encoded by such polynucleotides are further provided. Recombinant expression vectors comprising any of the above polynucleotides, and host cells transformed or transfected with such expression vectors, are provided within related aspects.

Within other aspects, the present invention provides antisense polynucleotides comprising at least 10 nucleotides complementary to a polynucleotide as described above.

Within further aspects, pharmaceutical compositions are provided, comprising: (a) a polypeptide or polynucleotide as described above; and (b) a physiologically acceptable carrier.

The present invention further provides, within other aspects, methods for phosphorylating a MEK3 polypeptide, comprising contacting a MEK3 polypeptide with a polypeptide according to claim as described above, thereby phosphorylating the MEK3 polypeptide.

Within further aspects, the present invention provides methods for activating a member of a stress-responsive MAP kinase pathway in an organism, comprising administering to an organism a polypeptide as described above, and thereby activating a member of a stress-responsive MAP kinase pathway.

Within other aspects, methods are provided for phosphorylating a MEK3 polypeptide comprising contacting a MEK3 polypeptide with a polypeptide as described above, and thereby phosphorylating the MEK3 polypeptide.

The present invention further provides methods for activating a member of a stress-responsive MAP kinase pathway in an organism, comprising administering to an organism a polypeptide as described above, and thereby activating a member of the stress-responsive MAP kinase pathway.

Within further aspects, the present invention provides methods for screening for an agent that modulates signal transduction via a stress-responsive MAP kinase pathway, comprising: (a) contacting a candidate agent with a polypeptide as described above; and (b) subsequently measuring the ability of the polypeptide to modulate the activity of a MEK3 polypeptide, and thereby evaluating the ability of the compound to modulate signal transduction via a stress-responsive MAP kinase pathway.

The present invention further provides, within other aspects, monoclonal antibodies and antigen-binding fragments thereof that specifically bind to a polypeptide as described above. Such monoclonal antibodies or fragments thereof may inhibit the phosphorylation of MEK3 by the polypeptide. Pharmaceutical compositions comprising: (a) an antibody or antigen-binding fragment thereof as described above; and (b) a physiologically acceptable carrier are also provided.

Within other aspects, the present invention provides methods for treating a patient afflicted with a disease associated with a stress-responsive MAP kinase pathway, comprising administering to a patient a compound that modulates the phosphorylation of MEK3. Within certain embodiments, the compound comprises a monoclonal antibody or antigen-binding fragment thereof or a nucleotide sequence. Within such methods, the compound may inhibit phosphorylation of MEK3 and the disease may be inflammation, an autoimmune disease, cancer or a degenerative disease. Alternatively, the compound may enhance the phosphorylation of MEK3 and the disease may be insulin-dependent diabetes or a neurodegenerative disease.

Within other aspects, methods are provided for determining the presence or absence of TAO kinase activity in a sample, comprising evaluating the ability of the sample to phosphorylate a MEK3 polypeptide, and thereby determining the presence or absence of TAO kinase activity in the sample.

Within related aspects, kits are provided for detecting TAO kinase activity in a sample, comprising a MEK3 polypeptide in combination with a suitable buffer.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1 presents the nucleotide and predicted amino acid sequence of a representative TAO1 kinase (SEQ ID NOs: 1 and 2).

FIG. 2 presents a comparison of the catalytic domains of TAO1 (residues 1–273 of SEQ ID NO:2), TAO2 (residues 1–273 of SEQ ID NO:4), STE20 (SEQ ID NO:17) and the *C. elegans* homolog (ceTAO) (SEQ ID NO:18). The catalytic domains were aligned by eye and the conserved amino acids bolded. The domains are indicated with roman numerals.

FIGS. 4A and 4B are Northern blots in which RNAs made from various human brain and spinal cord sections were hybridized to a TAO1-specific probe. Shown below each blot is the result of its hybridization to an actin probe. The lanes are as follows: 1, amygdala, 2, caudate nucleus, 3, corpus callosum, 4, hippocampus, 5, whole brain, 6, substantia nigra, 7, subthalamic nucleus, 8, thalamus, 9, cerebellum, 10, cerebral cortex, 11, medulla, 12, spinal cord, 13, occipital lobe, 14, frontal lobe, 15, temporal lobe, 16, putamen.

FIGS. 5A–5C are immunoblots. In FIG. 5A, human embryonic kidney 293 cells were transiently transfected with either vector or pCMV5TAO1(HA)$_3$, and 24 hours later lysates were immunoblotted with a monoclonal antibody directed against the HA epitope. TAO1 is indicated by the arrow. In FIG. 5B, the TAO1 proteins purified from Sf9 cells were immunoblotted with an antibody directed against the MRGS(H)$_6$ epitope. In FIG. 5C, 50 ng of (His)$_6$TAO1 was immunoblotted with polyclonal antisera P820 directed against a TAO1 peptide. An equal amount was blotted with the preimmune serum for P820.

FIG. 12 presents an alignment of a human retina cDNA EST (sbjct; SEQ ID NO:5) with nts. 2341–2754 of the rat TAO1 kinase sequence (query) provided in FIG. 1 (SEQ ID NO:1).

FIG. 13 presents an alignment of a human retina cDNA EST (sbjct; SEQ ID NO:6) with nts. 964–651 of the rat TAO1 kinase sequence (query) provided in FIG. 1 (SEQ ID NO:1).

FIG. 14 presents an alignment of a human retina cDNA EST (sbjct; SEQ ID NO:7) with nts. 2792–2423 of the rat TAO1 kinase sequence (query) provided in FIG. 1 (SEQ ID NO:1).

FIGS. 15A–15B presents an alignment of a human retina cDNA EST (sbjct; SEQ ID NO:8) with nts. 2248–2437 of the rat TAO1 kinase sequence (query) provided in FIG. 1 (SEQ ID NO:1). FIG. 15B presents an alignment of a human retina cDNA EST (sbjct; SEQ ID NO:9) with nts. 2437–2501 of the rat TAO1 kinase sequence (query) provided in FIG. 1 (SEQ ID NO:1).

FIG. 16 presents an alignment of a human retina cDNA EST (sbjct; SEQ ID NO:10) with nts. 2087–2305 of the rat TAO1 kinase sequence (query) provided in FIG. 1 (SEQ ID NO:1).

FIGS. 17A–17B presents an alignment of a human retina cDNA EST (sbjct; SEQ ID NO:1) with nts. 3228–3312 of the rat TAO1 kinase sequence (query) provided in FIG. 1 (SEQ ID NO:1). FIG. 17B presents an alignment of a human retina cDNA EST (sbjct; SEQ ID NO:12) with nts. 3200–3245 of the rat TAO1 kinase sequence (query) provided in FIG. 1 (SEQ ID NO:1).

FIG. 18 presents an alignment of a human retina cDNA EST (sbjct; SEQ ID NO:13) with nts. 739–854 of the rat TAO1 kinase sequence (query) provided in FIG. 1 (SEQ ID NO:1).

FIGS. 19A–19B presents an alignment of a human retina cDNA EST (sbjct; SEQ ID NO:14) with nts. 526–643 of the rat TAO1 kinase sequence (query) provided in FIG. 1 (SEQ ID NO:1). FIG. 19B presents an alignment of a human retina cDNA EST (sbjct; SEQ ID NO:15) with nts. 187–296 of the rat TAO1 kinase sequence (query) provided in FIG. 1 (SEQ ID NO:1).

FIG. 20 presents an alignment of a human retina cDNA EST (sbjct; SEQ ID NO:16) with nts. 866–733 of the rat TAO1 kinase sequence (query) provided in FIG. 1 (SEQ ID NO:1).

DETAILED DESCRIPTION OF THE INVENTION

Figure 3A:
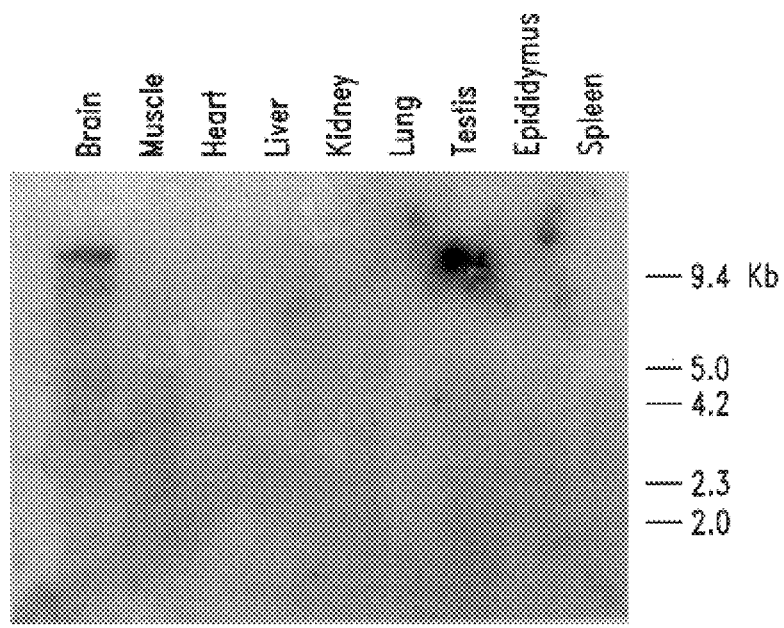
FIGS. 3A and 3B are Northern blots, showing TAO1 (FIG. 3A) and TAO2 (FIG. 3B) expression is various tissues. Various rat poly-A+ RNAs were probed, as indicated. Equal loading of RNA was verified by hybridizing the blot to an actin probe (not shown).

As noted above, the present invention is generally directed to compounds and methods for modulating (i.e., stimulating or inhibiting) the activity of MAP/ERK family members such as the MAP/ERK kinase MEK3. Compounds that activate such MEKs generally stimulate MEK phosphorylation. Such compounds include Ste20p homologs referred to herein as TAO polypeptides (i.e., TAO1, TAO2 or a variant of TAO1 or TAO2 that retains the ability to stimulate MEK3 phosphorylation at a level that is not substantially lower than the level stimulated by the native protein). Alternatively, a compound that activates MEK3 may comprise a polynucleotide that encodes a TAO polypeptide. Within other embodiments, compositions that stimulate MEK3 phosphorylation (thereby activating MEK3) may also, or alternatively, include one or more agents that stimulate TAO polypeptide expression or kinase activity. Such agents include, but are not limited to, stress-inducing agents (e.g., DNA-damaging agents). Additional such agents may be identified by combining a test compound with a TAO polypeptide in vitro and evaluating the effect of the test compound on the kinase activity of the polypeptide using, for example, a representative assay described herein.

Compositions that inhibit the activity of MEKs generally inhibit MEK phosphorylation. Such compositions may include one or more agents that inhibit or block TAO polypeptide activity, such as an antibody that inhibits the kinase activity of a TAO polypeptide, a competing peptide that represents the substrate binding domain of a TAO protein or a phosphorylation motif of the MEK3 substrate, an antisense polynucleotide or ribozyme that interferes with transcription and/or translation of a TAO polypeptide, a molecule that inactivates a TAO polypeptide by binding to the polypeptide, a molecule that binds to the TAO substrate and prevents phosphorylation by a TAO polypeptide or a molecule that prevents transfer of phosphoryl groups from the kinase to the substrate. Agents that inhibit TAO polypeptide kinase activity may be identified by combining a test compound with a TAO polypeptide in vitro and evaluating the activity of the TAO polypeptide using a TAO kinase assay.

TAO Polynucleotides

Any polynucleotide that encodes a TAO polypeptide, or a portion or variant thereof as described herein, is encompassed by the present invention. Such polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a TAO polynucleotide may, but need not, be linked to other molecules and/or support materials.

Native TAO DNA sequences, or portions thereof, may be isolated using any of a variety of hybridization or amplification techniques, which are well known to those of ordinary skill in the art. Within such techniques, probes or primers may be designed based on the TAO sequences provided herein, and may be purchased or synthesized. Libraries from any suitable tissue (e.g., brain) may be screened. An amplified portion or partial cDNA molecule may then be used to isolate a full length gene from a genomic DNA library or from a cDNA library, using well known techniques. Alternatively, a full length gene can be constructed from multiple PCR fragments.

Nucleic acid sequences corresponding to the native rat TAO polypeptides TAO1 and TAO2 are provided in SEQ ID NO:1 and SEQ ID NO:3, respectively. One preferred variant of TAO1 comprises amino acids 1–416 of SEQ ID NO:1. The predicted TAO1 open reading frame encodes a polypeptide of 1001 amino acids with a calculated molecular mass of 134 kD. TAO1 comprises an amino-terminal catalytic domain and an extensive carboxy-terminal region that has several distinguishing features, such as a possible nucleotide binding site and acidic stretch just carboxy-terminal to the catalytic domain, as well as two serine-rich regions. The TAO1 catalytic domain extends 263 amino acids from amino acid 25 to 288 with all 11 of the typical protein kinase subdomains conserved. There are two glutamate residues between TAO1 subdomains II and IV; the second glutamate at amino acid 76 contained in the sequence KEVK is most likely to represent subdomain III (flanks et al., *Science* 241:42–52, 1988). The features of the TAO1 catalytic domain are most similar to the serine/threonine family of protein kinases; subdomain VIb with the sequence HRDIK-AGN (SEQ ID NO:26) suggests that TAO1 is likely to be a serine/threonine protein kinase.

A partial sequence of the closely related gene TAO2 is provided in SEQ ID NOs:3 and 4. TAO2 has a similar arrangement of an amino-terminal kinase domain and a long carboxy-terminus, but differs in that it contains an acidic insert of 17 glutamate residues carboxy-terminal to the catalytic domain, and lacks the putative nucleotide binding site of TAO1.

The rat TAO1 and TAO2 transcripts are highly expressed in brain. Lower levels of TAO1 expression can be observed in heart and lung, with no detectable signal (using a Northern blot analysis as described herein) in skeletal muscle, liver, kidney, testis, epididymus and spleen.

The polynucleotides specifically recited herein, as well as full length polynucleotides comprising such sequences, other portions of full length polynucleotides, and sequences complementary to all or a portion of such full length molecules, are specifically encompassed by the present invention. In addition, TAO homologs from other species are specifically contemplated, and may generally be prepared as described herein for the rat homologs. In particular, within the context of the present invention, EST database sequences derived from retinal mRNAs have been identified that correspond to the human counterpart for TAO1. The sequences of these ESTs are provided in SEQ ID NOs:5–16. It will be readily apparent to those of ordinary skill in the art that a full length, native, human TAO1 polynucleotide may be identified based on such sequences, using for example, standard hybridization or amplification techniques. Such full length TAO1 sequences are contemplated by the present invention, as are polypeptides encoded by such sequences, and variants of the naturally occurring sequences as discussed herein.

Polynucleotide variants of the recited sequences may differ from a native TAO polynucleotide in one or more substitutions, deletions, insertions and/or modifications. Certain variants encode a polypeptide that retains the ability to stimulate MEK3 phosphorylation at a level that is not substantially lower than the level stimulated by the native protein. The effect on the properties of the encoded polypeptide may generally be assessed as described herein. Preferred variants contain nucleotide substitutions, deletions, insertions and/or modifications at no more than 20%, preferably at no more than 10%, of the nucleotide positions. Certain variants are substantially homologous to a native gene, or a potion or complement thereof. Such polynucleotide variants are capable of hybridizing under moderately stringent conditions to a naturally occurring DNA sequence encoding a TAO protein (or a complementary sequence). Suitable moderately stringent conditions include prewashing in a solution of 5× SSC, 0.5% SDS, 1.0 mM EDTA (pH 8.0); hybridizing at 50° C.–65° C., 5× SSC, overnight; followed by washing twice at 65° C. for 20 minutes with each of 2×, 0.5× and 0.2× SSC containing 0.1% SDS). Such hybridizing DNA sequences are also within the scope of this invention.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention.

As noted above, the present invention further provides antisense polynucleotides and portions of any of the above sequences. Such polynucleotides may generally be prepared by any method known in the art, including synthesis by, for example, solid phase phosphoramidite chemical synthesis. Alternatively, RNA molecules may be generated by in vitro or in vivo transcription of DNA sequences that are incorporated into a vector downstream of a suitable RNA polymerase promoter (such as T3, T7 or SP6). Certain portions of a TAO polynucleotide may be used to prepare an encoded polypeptide, as described herein. In addition, or alternatively, a portion may function as a probe (e.g., to detect TAO expression in a sample), and may be labeled by a variety of reporter groups, such as radionuclides, fluorescent dyes and enzymes. Such portions are preferably at least 10 nucleotides in length, and more preferably at least 20 nucleotides in length. Within certain preferred embodiments, a portion for use as a probe comprises a sequence that is unique to a TAO gene. A portion of a sequence complementary to a coding sequence (i.e., an antisense polynucleotide) may also be used as a probe or to modulate gene expression. DNA constructs that can be transcribed into antisense RNA may also be introduced into cells or tissues to facilitate the production of antisense RNA.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Additional initial, terminal and/or intervening DNA sequences that, for example, facilitate construction of readily expressed vectors may also be present. Suitable vectors may be obtained commercially or assembled from the sequences described by methods well-known in the art. Other elements that may be present in a vector will depend upon the desired use, and will be apparent to those of ordinary skill in the art.

Vectors as described herein may generally be transfected into a suitable host cell, such as a mammalian cell, by methods well-known in the art Such methods include calcium phosphate precipitation, electroporation and microinjection.

TAO Polypeptides

Polypeptides within the scope of the present invention comprise at least a portion of a TAO protein (e.g., TAO1 or TAO2) or variant thereof, where the portion is immunologically and/or biologically active. Preferred variants retain the ability to stimulate MEK3 phosphorylation at a level that is not substantially lower than the level stimulated by the native protein. A polypeptide may further comprise additional sequences, which may or may not be derived from a native TAO protein. Such sequences may (but need not) possess immunogenic or antigenic properties and/or a biological activity.

A polypeptide "variant," as used herein, is a polypeptide that differs from a native protein in substitutions, insertions, deletions and/or amino acid modifications, such that the immunogenic and/or biological properties of the native protein are not substantially diminished. A variant preferably retains at least 80% sequence identity to a native sequence, more preferably at least 90% identity, and even more preferably at least 95% identity. Within certain preferred embodiments, such variants contain alterations at no more than 10% of the amino acid residues in the native polypeptide, such that the ability of the variant to stimulate MEK3 phosphorylation is not substantially diminished. Guidance in determining which and how many amino acid residues may be substituted, inserted, deleted and/or modified without diminishing immunological and/or biological activity may be found using any of a variety of methods and computer programs known in the art. Properties of a variant may generally be evaluated by assaying the reactivity of the variant with, for example, antibodies as described herein and/or evaluating a biological property characteristic of the native protein.

A polypeptide is "immunologically active," within the context of the present invention if it is recognized (i.e., specifically bound) by a B-cell and/or T-cell surface antigen receptor. Immunological activity may generally be assessed using well known techniques, such as those summarized in Paul, *Fundamental Immunology*, 3rd ed., 243–247 (Raven Press, 1993) and references cited therein. Such techniques include screening polypeptides derived from the native polypeptide for the ability to react with antigen-specific antisera and/or T-cell lines or clones, which may be prepared using well known techniques. An immunologically active portion of a TAO protein reacts with such antisera and/or T-cells at a level that is not substantially lower than the reactivity of the full length polypeptide (e.g., in an ELISA and/or T-cell reactivity assay). Such screens may generally be performed using methods well known to those of ordinary skill in the art, such as those described in Harlow and Lane, *Antibodies: A Laboratory Manual,* Cold Spring Harbor Laboratory, 1988. B-cell and T-cell epitopes may also be predicted via computer analysis.

Similarly, a polypeptide is "biologically active" if the ability to phosphorylate MEK3 and/or other MEKs is not substantially diminished within a representative in vitro assay as described in Example 3. Preferably, the ability of the polypeptide to phosphorylate MEK3 is not substantially diminished. As used herein, the term "not substantially diminished" means retaining an activity that is at least 90% of the activity of a native TAO protein. Appropriate assays designed to evaluate such activity may be designed based on existing assays known in the art, and on the representative assays provided herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes.

In general, modifications may be more readily made in non-critical regions, which are regions of the native sequence that do not substantially change the properties of the TAO protein. Non-critical regions may be identified by modifying the TAO sequence in a particular region and assaying the activity of the resulting variant in a kinase assay, using MEK3, MEK4, MEK6 or another MEK family member as a substrate, as described herein. Modifications may also be made in critical regions of a TAO protein, provided that the resulting variant retains the ability to stimulate MEK3 phosphorylation and/or an immunogenic property of the native protein. Inactive proteins may be created by modifying certain critical regions. One critical region comprises the aspartate 169 residue. Modification of that residue results in a catalytically defective mutant. Another critical region encompasses the lysine 57 residue. The effect of any modification on the ability of the variant to stimulate phosphorylation of MEK3 or other MEKs may generally be evaluated using any assay for TAO kinase activity, such as the representative assays described herein.

Variants of TAO proteins include constitutively active proteins. In general, activation of a TAO protein in vivo requires stimulation by a stimulus such as a stress-inducing agent. Constitutively active variants display the ability to stimulate MEK phosphorylation in the absence of such stimulation. Such variants may be identified using the representative in vivo assays for TAO kinase activity described herein.

TAO proteins may also be modified so as to render the protein constitutively inactive (i.e., unable to phosphorylate MEKs even when stimulated as described above). Such modifications may be identified using the representative assays described herein. Genes encoding proteins modified so as to be constitutively active or inactive may generally be used in replacement therapy for treatment of a variety of disorders, as discussed in more detail below.

Variants within the scope of this invention also include polypeptides in which the primary amino acid structure of a native protein is modified by forming covalent or aggregative conjugates with other polypeptides or chemical moieties such as glycosyl groups, lipids, phosphate, acetyl groups and the like. Covalent derivatives may be prepared, for example, by linking particular functional groups to amino acid side chains or at the N- or C-termini.

The present invention also includes polypeptides with or without associated native-pattern glycosylation. Polypeptides expressed in yeast or mammalian expression systems may be similar to or slightly different in molecular weight and glycosylation pattern than the native molecules, depending upon the expression system. Expression of DNA in bacteria such as *E. coli* provides non-glycosylated molecules. N-glycosylation sites of eukaryotic proteins are characterized by the amino acid triplet Asn-$A_1$-Z, where $A_1$ is any amino acid except Pro, and Z is Ser or Thr. Variants having inactivated N-glycosylation sites can be produced by techniques known to those of ordinary skill in the art, such as oligonucleotide synthesis and ligation or site-specific mutagenesis techniques, and are within the scope of this invention. Alternatively, N-linked glycosylation sites can be added to a polypeptide.

As noted above, polypeptides may further comprise sequences that are of related to an endogenous TAO protein. For example, an N-terminal signal (or leader) sequence may be present, which co-translationally or post-translationally directs transfer of the polypeptide from its site of synthesis to a site inside or outside of the cell membrane or wall (e.g., the yeast α-factor leader). The polypeptide may also comprise a linker or other sequence for ease of synthesis, purification or identification of the polypeptide (e.g., poly-His, hemagglutinin, glutathione-S-transferase or FLAG), or to enhance polypeptide stability or binding to a solid support. Protein fusions encompassed by this invention further include, for example, polypeptides conjugated to an immunoglobulin Fc region or a leucine zipper domain. All of the above protein fusions may be prepared by chemical linkage or as fusion proteins.

Also included within the present invention are alleles of a TAO protein. Alleles are alternative forms of a native protein resulting from one or more genetic mutations (which may be amino acid deletions, additions and/or substitutions), resulting in an altered mRNA. Allelic proteins may differ in sequence, but overall structure and function are substantially similar.

TAO polypeptides, variants and portions thereof may generally be prepared from nucleic acid encoding the desired polypeptide using well known techniques. To prepare an endogenous protein, an isolated cDNA may be used. To prepare a variant polypeptide, standard mutagenesis techniques, such as oligonucleotide-directed site-specific mutagenesis may be used, and sections of the DNA sequence may be removed to permit preparation of truncated polypeptides.

In general, any of a variety of expression vectors known to those of ordinary skill in the art may be employed to express recombinant polypeptides of this invention. Expression may be achieved in any appropriate host cell that has been transformed or transfected with an expression vector containing a DNA sequence that encodes a recombinant polypeptide. Suitable host cells include prokaryotes, yeast, baculovirus-infected insect cells and animal cells. Following expression, supernatants from host/vector systems which secrete recombinant protein or polypeptide into culture media may be first concentrated using a commercially available filter. Following concentration, the concentrate may be applied to a suitable purification matrix such as an affinity matrix or an ion exchange resin. One or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Various modified solid phase techniques are also available (e.g., the method of Roberge et al., *Science* 269:202–204, 1995). Equipment for automated synthesis of polypeptides is commercially available from suppliers such as Applied BioSystems, Inc. (Foster City, Calif.), and may be operated according to the manufacturer's instructions.

In general, polypeptides and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, polypeptides provided herein are isolated to a purity of at least 80% by weight, more preferably to a purity of at least 95% by weight, and most preferably to a purity of at least 99% by weight. In general, such purification may be achieved using, for example, the standard techniques of ammonium sulfate fractionation, SDS-PAGE electrophoresis, and affinity chromatography. A polynucleotide is considered to be isolated if, for example, it is cloned into a vector that is not a part of the natural environment.

Antibodies and Fragments Thereof

The present invention further provides antibodies, and antigen-binding fragments thereof, that specifically bind to a TAO polypeptide. As used herein, an antibody, or antigen-binding fragment, is said to "specifically bind" to a TAO polypeptide if it reacts at a detectable level (within, for example, an ELISA) with a TAO polypeptide, and does not react detectably with unrelated proteins. Antibodies may be polyclonal or monoclonal. Preferred antibodies are those antibodies that inhibit or block TAO activity in vivo and within a kinase assay as described herein. Other preferred antibodies (which may be used, for example, in immunokinase assays) are those that immunoprecipitate active TAO1 and/or TAO2.

Antibodies may be prepared by any of a variety of techniques known to those of ordinary skill in the art (see, e.g., Harlow and Lane, *Antibodies: A Laboratory Manual*, Cold Spring Harbor Laboratory, 1988). In one such technique, an immunogen comprising the polypeptide is initially injected into a suitable animal (e.g., mice, rats, rabbits, sheep and goats), preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for a TAO polypeptide may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual,* Cold Spring Harbor Laboratory, 1988) and digested by papain to yield Fab and Fc fragments. The Fab and Fc fragments may be separated by, for example, affinity chromatography on protein A bead columns.

Methods and Kits for Detecting TAO Polypeptides and TAO Kinase Activity

The present invention provides methods for detecting the level of TAO1 and/or TAO2 in a sample, as well as for detecting TAO kinase activity in a sample. The level of a TAO polypeptide or polynucleotide may generally be determined using a reagent that binds to the TAO protein, DNA or mRNA. To detect nucleic acid encoding a TAO protein, standard hybridization and/or PCR techniques may be employed using a nucleic acid probe or a PCR primer. Suitable probes and primers may be designed by those of ordinary skill in the art based on the TAO cDNA sequences provided herein. To detect TAO protein, the reagent is typically an antibody, which may be prepared as described herein.

There are a variety of assay formats known to those of ordinary skill in the art for using an antibody to detect a polypeptide in a sample. See, e.g., Harlow and Lane, *Antibodies: A Laboratory Manual,* Cold Spring Harbor Laboratory, 1988. For example, the antibody may be immobilized on a solid support such that it can bind to and remove the polypeptide from the sample. The bound polypeptide may then be detected using a second antibody that binds to the antibody/peptide complex and contains a detectable reporter group. Alternatively, a competitive assay may be utilized, in which polypeptide that binds to the immobilized antibody is labeled with a reporter group and allowed to bind to the immobilized antibody after incubation of the antibody with the sample. The extent to which components of the sample inhibit the binding of the labeled polypeptide to the antibody is indicative of the level of polypeptide within the sample. Suitable reporter groups for use in these methods include, but are not limited to, enzymes (e.g., horseradish peroxidase), substrates, cofactors, inhibitors, dyes, radionuclides, luminescent groups, fluorescent groups and biotin.

For detecting an active TAO protein in a sample, an immunokinase assay may be employed. Briefly, polyclonal or monoclonal antibodies may be raised against a unique sequence of a TAO protein (such as amino acid residues 296–315, 403–418, 545–563 or 829–848) using standard techniques. A sample to be tested, such as a cellular extract, is incubated with the anti-TAO antibodies to immunoprecipitate a TAO protein, and the immunoprecipitated material is then incubated with a substrate (e.g., MEK3) under suitable conditions for substrate phosphorylation. The level of substrate phosphorylation may generally be determined using any of a variety of assays, as described herein.

TAO kinase assays, for use in evaluating the polypeptide variants and other agents discussed herein, include any assays that evaluate a compound's ability to phosphorylate MEK3 or other MEKs, thereby rendering the MEK active (i.e., capable of phosphorylating in vivo substrates such as p38). MEKs such as MEK3 for use in such methods may be endogenous proteins or variants thereof, may be purified or recombinant, and may be prepared using any of a variety of techniques that will be apparent to those of ordinary skill in the art. For example, cDNA encoding MEK3 may be cloned by PCR amplification from a suitable human cDNA library, using polymerase chain reaction (PCR) and methods well known to those of ordinary skill in the art. MEK3 may be cloned using primers based on the published sequence (Derijard et al., *Science* 267:682–685, 1995). MEK3 cDNA may then be cloned into a bacterial expression vector and the protein produced in bacteria, such as *E. coli,* using standard techniques. The bacterial expression vector may, but need not, include DNA encoding an epitope such as glutathione-S transferase protein (GST) such that the recombinant protein contains the epitope at the N- or C-terminus.

A TAO kinase assay may generally be performed as described herein. Briefly, a TAO polypeptide may be incubated with MEK3 and [$\gamma$-$^{32}$P]ATP in a suitable buffer (such as 50 mM HEPES pH 8, 10 mM MgCl$_2$, 1 mM DTT, 100 $\mu$M ATP) for 60 minutes at 30° C. In general, approximately 50 ng to 1 $\mu$g of the polypeptide and 50 ng recombinant MEK3, with 2–7 cpm/fmol [$\gamma$-$^{32}$P]ATP, is sufficient. Proteins may then be separated by SDS-PAGE on 10% gels and subjected to autoradiography. Incorporation of [$^{32}$P]phosphate into MEK3 may be quantitated using techniques well known to those of ordinary skill in the art, such as with a phosphorimager. To evaluate the substrate specificity of polypeptide variants, a kinase assay may generally be performed as described above except that other MEK substrates (i.e., MEK1, 2, 4 or 6) are substituted for the MEK3.

To determine whether MEK3 phosphorylation results in activation, a coupled in vitro kinase assay may be performed using a substrate for MEK3, such as p38, with or without an epitope tag. p38 for use in such an assay may be prepared as described in Han et al., *J. Biol. Chem.* 271:2886–2891, 1996. Briefly, following phosphorylation of MEK3 as described above, the MEK3 (e.g., 0.1–10 ng) may be incubated with p38 (e.g., 10 $\mu$g/ml) and [$\gamma$-$^{32}$P]ATP in a kinase buffer as described herein. It should be noted that alternative buffers may be used and that buffer composition can vary without significantly altering kinase activity. Reactions may be separated by SDS-PAGE, visualized by autoradiography and quantitated using any of a variety of known techniques. Activated MEK3 will be capable of phosphorylating p38 at a level that is at least 5% above background using such an assay.

The present invention further provides kits for detecting TAO polypeptides and TAO kinase activity. Such kits may be designed for detecting the level of a TAO polypeptide or polynucleotide, or may detect phosphorylation of MEK3 in a direct kinase assay or a coupled kinase assay, in which the level of phosphorylation and/or the kinase activity of MEK3 may be determined. TAO polypeptides and TAO kinase activity may be detected in any of a variety of samples, such as eukaryotic cells, bacteria, viruses, extracts prepared from such organisms and fluids found within living organisms. In general, the kits of the present invention comprise one or more containers enclosing elements, such as reagents or buffers, to be used in the assay.

A kit for detecting the level of TAO polypeptide or polynucleotide typically contains a reagent that binds to TAO1 and/or TAO2 protein, DNA or RNA. To detect nucleic acid encoding a TAO polypeptide, the reagent may be a nucleic acid probe or a PCR primer. To detect a TAO protein, the reagent is typically an antibody. The kit also contains a reporter group suitable for direct or indirect detection of the reagent (i.e., the reporter group may be covalently bound to the reagent or may be bound to a second molecule, such as Protein A, Protein G, immunoglobulin or lectin, which is itself capable of binding to the reagent). Suitable reporter groups include, but are not limited to, enzymes (e.g., horseradish peroxidase), substrates, cofactors, inhibitors, dyes, radionuclides, luminescent groups, fluorescent groups and biotin. Such reporter groups may be used to directly or indirectly detect binding of the reagent to a sample component using standard methods known to those of ordinary skill in the art.

A kit for detecting TAO kinase activity based on measuring the phosphorylation of MEK3 generally comprises MEK3 in combination with a suitable buffer. A kit for detecting TAO kinase activity based on detecting MEK3 activity generally comprises MEK3 in combination with a suitable MEK3 substrate, such as p38. Optionally, the kit may additionally comprise a suitable buffer and/or material for purification of MEK3 after activation and before combination with substrate. Such kits may be employed in direct or coupled kinase assays, which may be performed as described above.

Methods for Identifying Binding Agents and Modulating Agents

The present invention further provides methods for identifying antibodies and other compounds that bind to and/or modulate the activity of a TAO polypeptide. To evaluate the effect of a candidate modulating agent on TAO polypeptide activity, a kinase assay may be performed as described above, except that the candidate modulating agent is added to the incubation mixture. Briefly, the reaction components, which include the composition to be tested and the TAO polypeptide or a polynucleotide encoding the kinase, are incubated under conditions sufficient to allow the components to interact. Subsequently, the effect of composition on kinase activity or on the level of a polynucleotide encoding the kinase is measured. The observed effect on the kinase may be either inhibitory or stimulatory. The increase or decrease in kinase activity can be measured by, for example, adding a radioactive compound such as $^{32}$P-ATP to the mixture of components, and observing radioactive incorporation into MEK3 or other suitable substrate for a TAO polypeptide, to determine whether the compound inhibits or stimulates kinase activity. A polynucleotide encoding the kinase may be inserted into an expression vector and the effect of a composition on transcription of TAO mRNA can be measured, for example, by Northern blot analysis.

Within such assays, the candidate agent may be preincubated with a TAO polypeptide before addition of ATP and substrate. Alternatively, the substrate may be preincubated with the candidate agent before the addition of kinase. Further variations include adding the candidate agent to a mixture of TAO polypeptide and ATP before the addition of substrate, or to a mixture of substrate and ATP before the addition of TAO polypeptide. Any of these assays can further be modified by removing the candidate agent after the initial preincubation step. In general, a suitable amount of antibody or other candidate agent for use in such an assay ranges from about 0.1 $\mu$M to about 10 $\mu$M. The effect of the agent on TAO kinase activity may then be evaluated by quantitating the incorporation of [$^{32}$P]phosphate into MEK3, as described above, and comparing the level of incorporation with that achieved using the TAO polypeptide without the addition of the candidate agent.

TAO kinase activity may also be measured in whole cells transfected with a reporter gene whose expression is dependent upon the activation of MEK3. For example, polynucleotides encoding a TAO polypeptide and a substrate (e.g., MEK3) may be cotransfected into a cell. The substrate may then be immunoprecipitated, and its activity evaluated in an in vitro assay. Alternatively, cells may be transfected with a ATF2-dependent promoter linked to a reporter gene such as luciferase. In such a system, expression of the luciferase gene (which may be readily detected using methods well known to those of ordinary skill in the art) depends upon activation of ATF2 by p38, which may be achieved by the stimulation of MEK3 with a TAO polypeptide. Candidate modulating agents may be added to the system, as described below, to evaluate their effect on TAO polypeptide activity.

Alternatively, a whole cell system may employ only the transactivation domain of ATF2 fused to a suitable DNA binding domain, such as GHF-1 or GAL4. The reporter system may then comprise the GH-luciferase or GAL4-luciferase plasmid. Candidate TAO protein modulating agents may then be added to the system to evaluate their effect on ATF2-specific gene activation.

In other aspects of the subject invention, methods for using the above polypeptides to phosphorylate and activate MEK3, peptide derivatives thereof or other MEK family members are provided. MEK substrate for use in such methods may be prepared as described above. In one embodiment, MEK3 may be phosphorylated in vitro by incubation with a TAO polypeptide and ATP in a suitable buffer as described above. In general, the amounts of the reaction components may range from about 0.1 $\mu$g to about 10 $\mu$g of TAO polypeptide, from about 0.1 $\mu$g to about 10 $\mu$g of recombinant MEK3, and from about 100 nM to about 1 mM (preferably about 100 pmol–30 nmol) of ATP. Phosphorylated proteins may then be purified by binding to GSH-sepharose and washing. The extent of MEK3 phosphorylation may generally be monitored by adding [$\gamma$-$^{32}$P] ATP to a test aliquot, and evaluating the level of MEK3 phosphorylation as described above. The activity of the phosphorylated MEK3 may be evaluated using a coupled in vitro kinase assay, as described above.

Once activated in vitro, MEK3 may be used, for example, to identify agents that inhibit the kinase activity of MEK3. Such inhibitory agents, which may be antibodies or drugs, may be identified using the coupled assay described above. Briefly, a candidate agent may be included in the mixture of MEK3 and p38, with or without pre-incubation with one or more components of the mixture, as described above. In general, a suitable amount of antibody or other agent for use in such an assay ranges from about 0.1 $\mu$M to about 10 $\mu$M. The effect of the agent on MEK3 kinase activity may then be evaluated by quantitating the incorporation of [$^{32}$P] phosphate into p38, as described above, and comparing the level of incorporation with that achieved using activated MEK3 without the addition of a candidate agent.

Within other aspects, TAO polypeptides may be used to identify one or more native upstream kinases (i.e., kinases that phosphorylate and activate TAO1 and/or TAO2 in vivo, or other signaling molecules that regulate TAO activity). TAO polypeptides may be used in a yeast two-hybrid system to identify interacting proteins. Alternatively, an expression library may be screened to identify cDNAs that encode proteins which phosphorylate a TAO polypeptide. Other methods for identifying such upstream kinases may also be employed, and will be apparent to those of ordinary skill in the art.

Pharmaceutical Compositions

For administration to a patient, one or more polypeptides, polynucleotides, antibodies and/or modulating agents are generally formulated as a pharmaceutical composition, which may be a sterile aqueous or non-aqueous solution, suspension or emulsion, and which additionally comprises a physiologically acceptable carrier (i.e., a non-toxic material that does not interfere with the activity of the active ingredient). Any suitable carrier known to those of ordinary skill in the art may be employed in a pharmaceutical composition. Representative carriers include physiological saline solutions, gelatin, water, alcohols, natural or synthetic oils, saccharide solutions, glycols, injectable organic esters such as ethyl oleate or a combination of such materials. Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, antimicrobial compounds, chelating agents such as EDTA or glutathione, adjuvants (e.g., aluminum hydroxide), inert gases and/or preservatives. Compositions of the present invention may also be formulated as a lyophilizate. Pharmaceutical compositions may also contain other compounds, which may be biologically active or inactive.

The compositions described herein may be administered as part of a sustained release formulation (i.e., a formulation such as a capsule that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or modulating agent dispersed in a carrier matrix and/or contained within a reservoir surrounded by a rate controlling membrane. Carriers for use within such formulations are biocompatible, and may also be biodegradable; preferably the formulation provides a relatively constant level of release. The amount of active compound contained within a sustained release formulation depends upon the site of implantation, the rate and expected duration of release and the nature of the condition to be treated or prevented.

Certain pharmaceutical compositions contain DNA encoding a polypeptide, antibody fragment or other modulating agent as described above (such that a TAO polypeptide, a variant thereof or a modulating agent is generated in situ) or an antisense polynucleotide. In such pharmaceutical compositions, the DNA may be present within any of a variety of delivery systems known to those of ordinary skill in the art, including nucleic acid, bacterial and viral expression systems, as well as colloidal dispersion systems, including liposomes. Appropriate nucleic acid expression systems contain the necessary DNA sequences for expression in the patient (such as a suitable promoter and terminating signal). The DNA may also be "naked," as described, for example, in Ulmer et al., *Science* 259:1745–1749, 1993.

Various viral vectors that can be used to introduce a nucleic acid sequence into the targeted patient's cells include, but are not limited to, vaccinia or other pox virus, herpes virus, retrovirus, or adenovirus. Techniques for incorporating DNA into such vectors are well known to those of ordinary skill in the art. Preferably, the retroviral vector is a derivative of a murine or avian retrovirus including, but not limited to, Moloney murine leukemia virus (MoMuLV), Harvey murine sarcoma virus (HaMuSV), murine mammary tumor virus (MuMTV), and Rous Sarcoma Virus (RSV). A retroviral vector may additionally transfer or incorporate a gene for a selectable marker (to aid in the identification or selection of transduced cells) and/or a gene that encodes the ligand for a receptor on a specific target cell (to render the vector target specific). For example, retroviral vectors can be made target specific by inserting a nucleotide sequence encoding a sugar, a glycolipid, or a protein. Targeting may also be accomplished using an antibody, by methods known to those of ordinary skill in the art.

Viral vectors are typically non-pathogenic (defective), replication competent viruses, which require assistance in order to produce infectious vector particles. This assistance can be provided, for example, by using helper cell lines that contain plasmids that encode all of the structural genes of the retrovirus under the control of regulatory sequences within the LTR, but that are missing a nucleotide sequence which enables the packaging mechanism to recognize an RNA transcript for encapsulation. Such helper cell lines include (but are not limited to) Ψ2, PA317 and PA12. A retroviral vector introduced into such cells can be packaged and vector virion produced. The vector virions produced by this method can then be used to infect a tissue cell line, such as NIH 3T3 cells, to produce large quantities of chimeric retroviral virions.

Another targeted delivery system for TAO polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). It has been shown that large unilamellar vesicles (LUV), which range in size from 0.2–4.0 $\mu$m can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques* 6:882, 1988).

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

Routes and frequency of administration, as well as polypeptide, modulating agent or nucleic acid doses, will vary from patient to patient. In general, the pharmaceutical compositions may be administered intravenously, intraperitoneally, intramuscularly, subcutaneously, intracavity or transdermally. Between 1 and 6 doses may be administered daily. A suitable dose is an amount of polypeptide or DNA that is sufficient to show improvement in the symptoms of a patient afflicted with a disease associated with a stress-responsive MAP kinase pathway. Such improvement may be detected based on a determination of relevant cytokine levels (e.g., IL-2, IL-8), by monitoring inflammatory responses (e.g., edema, transplant rejection, hypersensitivity) or through an improvement in clinical symptoms associated with the disease. In general, the amount of polypeptide present in a dose, or produced in situ by DNA present in a dose, ranges from about 1 μg to about 250 μg per kg of host, typically from about 1 μg to about 60 μg. Suitable dose sizes will vary with the size of the patient, but will typically range from about 10 mL to about 500 mL for 10–60 kg animal.

Therapeutic Applications

The above polypeptides, polynucleotides and/or modulating agents may be used to phosphorylate (and thereby activate) MEK3, or to inhibit such phosphorylation, in a patient. As used herein, a "patient" may be any mammal, including a human, and may be afflicted with a disease associated with a stress-responsive MAP kinase pathway, or may be free of detectable disease. Accordingly, the treatment may be of an existing disease or may be prophylactic. Diseases associated with a stress-responsive MAP kinase pathway include any disorder which is etiologically linked to a TAO protein kinase activity, including immune-related diseases (e.g., inflammatory diseases, autoimmune diseases, malignant cytokine production or endotoxic shock), cell growth-related diseases (e.g., cancer, metabolic diseases, abnormal cell growth and proliferation or cell cycle abnormalities) and cell regeneration-related diseases (e.g. cancer, degenerative diseases, trauma, environmental stress by heat, UV or chemicals or abnormalities in development and differentiation). Immunological-related cell proliferative diseases such as osteoarthritis, ischemia, reperfusion injury, trauma, certain cancers and viral disorders, and autoimmune diseases such as rheumatoid arthritis, diabetes, multiple sclerosis, psoriasis, inflammatory bowel disease, and other acute phase responses may also be treated.

Treatment includes administration of a composition or compound which modulates the kinase activity of TAO1 and/or TAO2. Such modulation includes the suppression of TAO expression and/or activity when it is over-expressed, or augmentation of TAO expression and/or activity when it is under-expressed. Modulation may also include the suppression of phosphorylation of MEK3 or related kinases.

As noted above, antibodies, polynucleotides and other agents having a desired effect on TAO expression and/or activity may be administered to a patient (either prophylactically or for treatment of an existing disease) to modulate the activation of MEK3 in vivo. For example, an agent that decreases TAO activity in vivo may be administered to prevent or treat inflammation, autoimmune diseases, cancer or degenerative diseases. In particular, such agents may be used to prevent or treat insulin-resistant diabetes, metabolic disorders and neurodegenerative diseases. In general, for administration to a patient, an antibody or other agent is formulated as a pharmaceutical composition as described above. A suitable dose of such an agent is an amount sufficient to show benefit in the patient based on the criteria noted above.

The following Examples are offered by way of illustration and not by way of limitation.

EXAMPLES

Example 1

Cloning and Sequencing cDNA Encoding TAO1 and TAO2

This Example illustrates the cloning of cDNA molecules encoding the rat Ste20p-related protein kinases TAO1 and TAO2, and the identification of the human TAO1 homolog.

First-strand cDNA from adult rat brain was used as the template in the first round of PCR with degenerate oligonucleotide primers derived from the Ste20p sequence, 5'-GACGCTGGATCCAA(AG)AT(ACT)GGICA(AG) GGIGC-3' (SEQ ID NO:19) and 5'-GGIGTICC(AG) TTIGTIGCIAT-3' (SEQ ID NO:20). A portion of the product of this reaction was used as the template in a second round of PCR with nested primers, also derived from the Ste20p sequence, 5'-AA(AG)GA(AG)CAIATI(CA)TIAA(CT)GA (AG)AT-3' (SEQ ID NO:21) and 5'-GACGCTGAATTCAC (CT)TCIGGIGCCATCCA-3' (SEQ ID NO:22). The resulting 420 base product was labeled with [α-$^{32}$P]dCTP by random-priming, and used to probe approximately 1×10$^6$ plaques of an oligo(dT) and random-primed λZAP library generated from adult rat forebrain RNA. In excess of 100 positive clones were obtained; of those sequenced, all contained regions of overlap with the original PCR product. A full length TAO1 sequence was assembled from two overlapping cDNAs, using the Sacd site at nucleotide 50 to insert a fragment of TAO1 cDNA including nucleotides 50 to 3003. The full length TAO1 sequence is shown in FIG. 1 and SEQ ID NO:1.

The TAO1 open reading frame encodes 1001 amino acids, with a calculated molecular mass of 134 kDa. The presumed initiator codon begins at base 121 and is preceded by an in-frame stop codon at base 106. The longest 5' UTR obtained was 600 nucleotides in length, and the longest 3' UTR was 1200 nucleotides. None of the clones analyzed contained a poly-A track.

As is the case with most protein kinases, TAO1 can be divided into regions based on amino acid sequence comparison to other protein kinases. TAO1 is composed of an amino-terminal catalytic domain and an extensive carboxy-terminal region that has several distinguishing features, such as a possible nucleotide binding site and acidic stretch just carboxy-terminal to the catalytic domain, as well as two serine-rich regions. TAO1 does not appear to contain the leucine zipper motifs found in the MLK subfamily of kinases.

The TAO1 catalytic domain extends 263 amino acids from amino acid 25 to 288 with all 11 of the typical protein kinase subdomains conserved. There are two glutamate residues between TAO1 subdomains II and IV; the second glutamate at amino acid 76 contained in the sequence KEVK is most likely to represent subdomain III (Hanks et al., Science 241:42–52, 1988). The features of the TAO1 catalytic domain are most similar to the serine/threonine family of protein kinases; subdomain VIb with the sequence HRDIKAGN suggests that TAO1 is likely to be a serine/threonine protein kinase.

When using FASTA (GCG, Wisconsin Package) to align TAO1 with sequences from the databases, the TAO1 catalytic domain shows the highest degree of identity to a C. elegans putative serine/threonine protein kinase (accession number U32275), to which it has 63% identity and 79% similarity. That sequence appears to represent the C. elegans homolog of TAO1, and is shown as ceTAO in FIG. 2. The TAO1 catalytic domain is 39% identical to Ste20p and 40% identical to the catalytic domains of the p21-activated kinases PAK1 and PAK2. The catalytic domain of TAO1 is only 31% identical to the mixed lineage kinase MLK1, and 33% identical to dual leucine zipper-bearing kinase (DLK), also known as MLK2. Thus, TAO1 appears to be more closely related to the STE20-like kinases than to the MLK family. TAO1 is also related to germinal center kinase (GCK) and mammalian Ste20-like kinase 1 (MST1), with 42% and 45% identity respectively in the catalytic domains.

The TAO1 sequence has similarity with that of the MEK kinase MEKK1. Although the overall identity between the catalytic domains of TAO1 and MEKK is only 33%, the identity of the carboxy-terminal half of their catalytic domains is higher (42%).

In the process of screening the cDNA library for clones near the 5' end of TAO1, multiple clones representing a second closely related gene (TAO2) were identified. The TAO2 sequence is provided in SEQ ID NO:3, with the predicted amino acid sequence shown in SEQ ID NO:4 and FIG. 2. TAO2 is highly related to TAO1, and has a similar arrangement of an amino-terminal kinase domain and a long carboxy-terminus, but differs in that it contains an acidic insert of 17 glutamate residues carboxy-terminal to the catalytic domain, and lacks the putative nucleotide binding site of TAO1.

Sequences from EST databases derived from retinal mRNAs revealed the human counterpart for TAO1. The EST sequences identified are provided in SEQ ID NOs:5–16, and the alignments of these sequences with the rat TAO1 sequence are provided in FIGS. 12–20.

The Fasta program was used to compare the percent amino acid identities of several protein kinase catalytic domains, and the results are presented in Table 1, below.

TABLE 1

|  | TAO1 |  |  |  |  |  |  |
|---|---|---|---|---|---|---|---|
| TAO2 | 90 | TAO2 |  |  |  |  |  |
| ceTAO | 65 | 61 | ceTAO |  |  |  |  |
| STE20d | 40 | 39 | 37 | STE20 |  |  |  |
| GCK | 43 | 42 | 35 | 40 | GCK |  |  |
| MLK1 | 32 | 30 | 27 | 30 | 29 | MLK1 |  |
| MST1 | 47 | 43 | 42 | 42 | 47 | 28 | MST1 |
| MEKK1 | 34 | 33 | 27 | 30 | 30 | 30 | 29 |

To assess the expression of TAO1 in transfected cells, full-length, HA-tagged TAO1 cDNA was transfected into human embryonic kidney 293 cells. A protein of approximately 140 kDa could be detected by Western blotting with an antibody directed against the HA epitope (FIG. 5A). The observed molecular mass of the protein is in good agreement with the mass predicted from the cDNA sequence.

Example 2

In vivo Expression of TAO1 and TAO2

This Example illustrates the expression of TAO1 and TAO2 in a variety of adult rat and human tissues, as determined by Northern blot analysis.

Total RNA isolated from various adult male rat tissues was selected for poly-A+ RNA with oligo(dT)cellulose (Collaborative Biomedical Products) according to the manufacturers protocols, and 5 µg of each RNA was subjected to Northern analysis. The PCR-generated 420 base fragment derived from the catalytic domain of TAO1 (described above) was labeled with [$\alpha$-$^{32}$P]dCTP by random-priming and used to probe the Northern blot. Hybridization was at 42° C., followed by washing at 55° C. in 0.2%SSC/ 0.1%SDS. Integrity of the mRNA was confirmed by hybridization to an actin probe. The TAO1 probe hybridized predominately to an mRNA species of approximately 12 kb, and less strongly to another of approximately 10 kb (FIG. 3A). Of the rat tissues examined, brain clearly showed the strongest hybridization signal. On prolonged exposure, heart and lung revealed weak hybridization signals, while in skeletal muscle, liver, kidney, testis, epididymus, and spleen no signal was detected.

To assess the expression pattern of TAO2, the rat tissue Northern blot was stored until the hybridization signal for TAO1 was not seen on a two week exposure at –80° C. A fragment from the catalytic domain of TAO2 was labeled with [$\alpha$-$^{32}$P]dCTP by random priming, and used to probe the Northern under the same hybridization and washing conditions described above for TAO1.

Figure 3B:
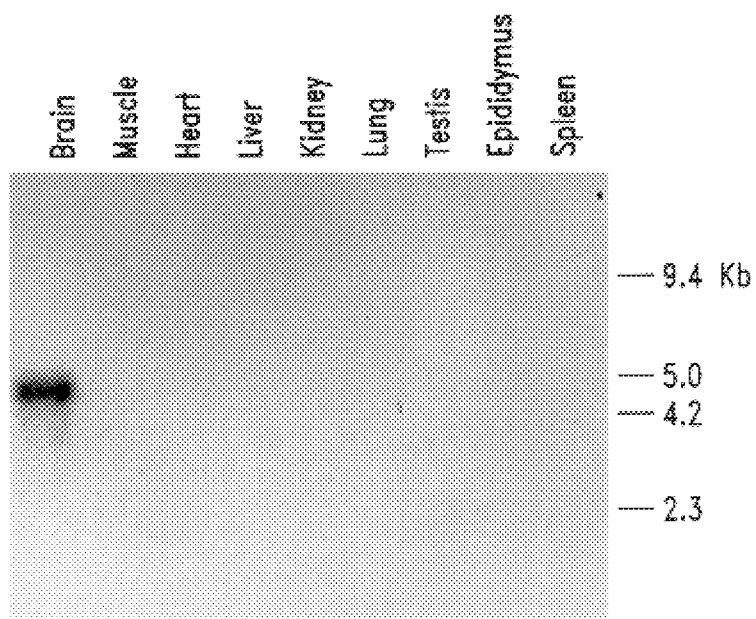

When the same rat tissue Northern blot was probed with a fragment of the catalytic domain of TAO2, the strongest hybridization signal was also seen in brain. The size of the transcript hybridizing to the TAO2 probe was smaller than that seen for TAO1, at 5 kb (FIG. 3B).

A probe from the non-catalytic carboxy-terminus of TAO1 (corresponding to nucleotides 1555 to 2632 of TAO1 (see FIG. 1)) was used for all additional Northern analyses because it is less likely to hybridize to TAO2 mRNA. This probe from the carboxy-terminus of TAO1 was used to assess the expression pattern in sections of human brain (Clontech). Hybridizations were performed at 68° C. in Clontech ExpressHyb buffer, and washed at 55° C. as per the manufacturer's instructions.

The strongest hybridization signals were seen in amygdala, corpus callosum, hippocampus, and substantia nigra, and each of these was stronger than that seen in whole brain (FIG. 4A). Weaker signals were seen in caudate nucleus, subthalamic nucleus and thalamus. A second human brain Northern hybridized to the same probe showed strong hybridization signals in cerebellum, putamen and occipital, frontal and temporal lobes, but much weaker signals in cerebral cortex, medulla and spinal cord (FIG. 4B).

Example 3

Kinase Activity and Substrate Specificity of TAO1

This Example illustrates the kinase activity and substrate specificity of TAO1, in in vitro and in vivo assays.

To determine whether TAO1 is active as a protein kinase, two constructs were employed. pCMV5TAO1-HA$_3$ and pCMV5TAO1(1–416)-HA, were generated by cloning the cDNAs encoding these TAO1 polypeptides into the pCMV5 mammalian expression vector. Oligonucleotide primers were used with TAO1 cDNA as template to amplify a 1247 base pair DNA product encoding amino acids 1 to 416. This fragment contains all 11 of the kinase subdomains (with the initial methionine deleted). The resulting constructs were transfected into human embryonic kidney 293 cells, and the recombinant, tagged proteins immunoprecipitated with an antibody directed against the HA epitope.

In vitro kinase assays were generally performed as follows. Kinase assays contained: 50 mM Hepes, pH 8, 10 mM MgCl$_2$, 1 mM DTT, 100 µM ATP, [$\gamma$-$^{32}$ P]ATP (at a final concentration of 2–7 cpm/fmol), and unless otherwise noted, reactions were incubated at 30° C. for 60 minutes in a 30 μl volume. Protein kinase substrates such as myelin basic protein were added at a final concentration of 0.5 mg/ml. Reactions were halted by the addition of 10μl 5× Laemmli buffer, followed by boiling, and 20 μl were analyzed by SDS-PAGE and autoradiography. For linked kinase assays, 50–250 ng of recombinant TAO1 protein was incubated with 50 ng of each of the bacterially expressed MEK proteins in a 30 μl reaction volume for 60 minutes at 30° C., and then 5 μl of this reaction was added to a second reaction mix containing bacterially expressed (His)$_6$p38 or GST-SAPKβ at a final concentration of 10 μg/ml. Recombinant MEK proteins were kindly provided by Andrei Khokhlatchev and Megan Robinson, and may be prepared as described by Robinson et al., *J. Biol. Chem.* 271:29734–29739, 1996 and references cited therein. Within such assays, both TAO1 (1–416) and full-length TAO1 were able to phosphorylate MBP in immune complex kinase reactions.

To quantitate the activity of more highly purified TAO1, TAO1(1–416), full-length TAO1 and full-length TAO1 (D169A) were expressed with an amino-terminal hexahistidine tag in Sf9 cells. TAO1(D169A) is a catalytically defective TAO1 mutant, which was created by changing aspartic acid 169 to an alanine (D169A) with PCR, and cloning the resulting construct into the pCMV5 mammalian expression vector. These constructs were prepared with either a single hemagglutinin (HA) epitope tag at the amino-terminus, a triple HA epitope tag at the carboxy-terminus, or a myc epitope tag at the amino-terminus.

The recombinant, hexa-histidine tagged TAO1, TAO1 (1–416), and TAO1(D169A) were expressed in *Spodoptera frugiperda* (Sf9) cells. Cells were lysed by douncing in 50 mM sodium phosphate, pH 8.5, 1 mM DTT, 1 mM PMSF, and 1 mg/ml each leupeptin, pepstatin A, and aprotinin. After centrifugation at 30,000×g for 30 minutes, the supernatant was applied to a Ni$^{2+}$-NTA agarose (Qiagen) column pre-equilibrated with the same buffer. The column was then washed with 50 column volumes of buffer, and eluted with a 20 ml gradient of 0 to 250 mM imidazole, all in the above buffer. Fractions containing recombinant TAO1 proteins were detected in fractions by Western blotting with an antibody to the MRGS(H)$_6$ epitope (Qiagen), and appropriate fractions were pooled and dialyzed to remove the imidazole.

(His)$_6$TAO1(1–416) expressed as a single 57 kDa band (FIG. 5B). Both the (His)$_6$TAO1 and (His)$_6$TAO1(D169A) recombinant proteins migrated as 140 kDa bands, although the D169A mutant appears to be more subject to degradation. (His)$_6$TAO1(1–416) phosphorylates MBP with a specific activity of 1 μmolmin$^{-1}$mg$^{-1}$ in the presence of 1 mM ATP. Full-length (His)$_6$TAO1 exhibits MBP phosphorylating activity that is comparable to the 1–416 truncation mutant, while the activity of TAO1(D169A) is reduced to 90% of that of the wild-type protein. (His)$_6$TAO1(1–416) was also able to phosphorylate α-casein, histone 1, and histone 7.

Figure 6:
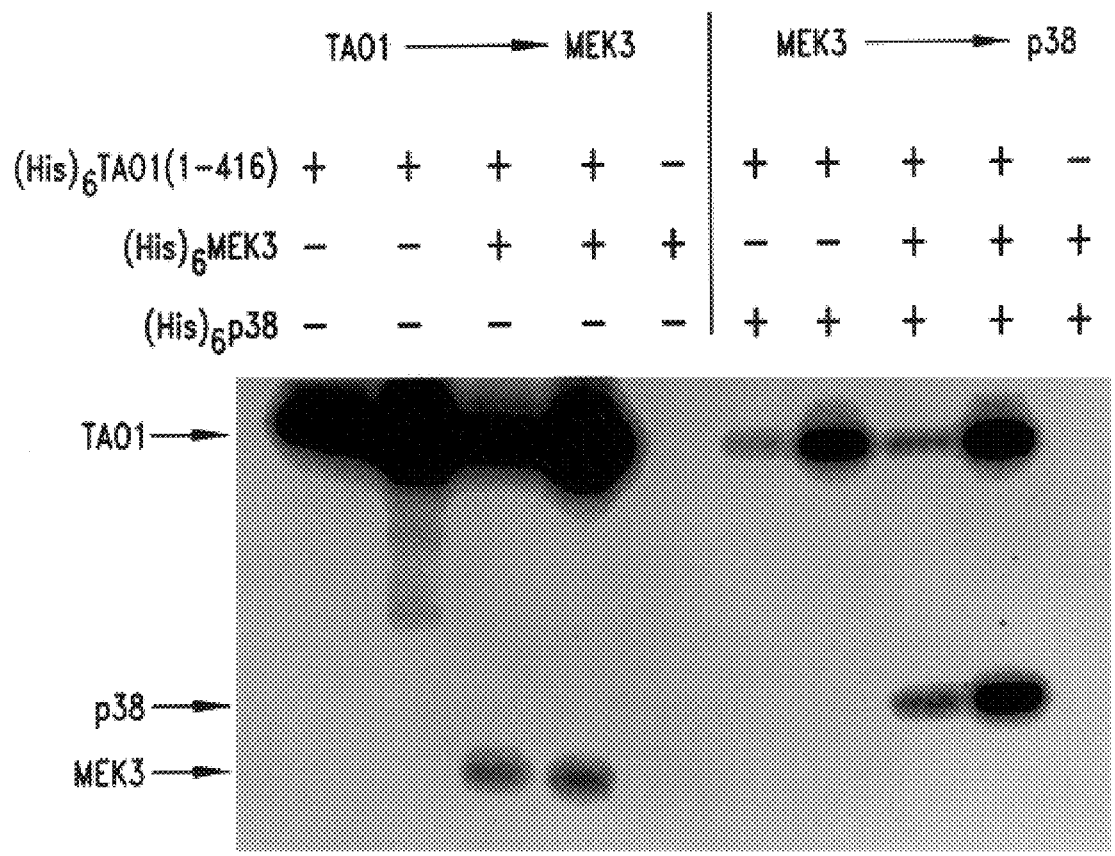
FIG. 6 is an autoradiogram showing the results of a representative in vitro linked kinase assay to estimate MEK activation by TAO1. Either 50 ng (lanes 1 and 3) or 250 ng (lanes 2 and 4) of (His)$_6$TAO1(1–416) was incubated with 50 ng of (His)$_6$MEK3 for one hour at 30° in the presence of Mg/ATP, after which a portion of the each reaction was added to a second reaction containing (His)6p38. After a one hour incubation, the reactions were subjected to SDS-PAGE and autoradiography.

To determine whether TAO1 activates one or more of the known MEKs, (His)$_6$TAO1(1–416) was incubated with bacterially produced MEK for one hour in the presence of Mg$^{2+}$ and [γ-$^{32}$P]ATP. A portion of this reaction was then transferred to a similar reaction containing the appropriate bacterially expressed MEK substrate, (His)$_6$ERK2K52R for MEK1 and MEK2, (His)$_6$p38 for MEK3 and MEK6, and (His)$_6$p38 and GST-SAPKβ for MEK4. After a one hour incubation, the phosphoproteins were separated by SDS-PAGE. Autoradiography revealed that (His)$_6$TAO1(1–416) phosphorylated and activated (His)$_6$MEK3, and enhanced the ability of MEK3 to phosphorylate p38 by approximately 100-fold (FIG. 6).

Figure 7:
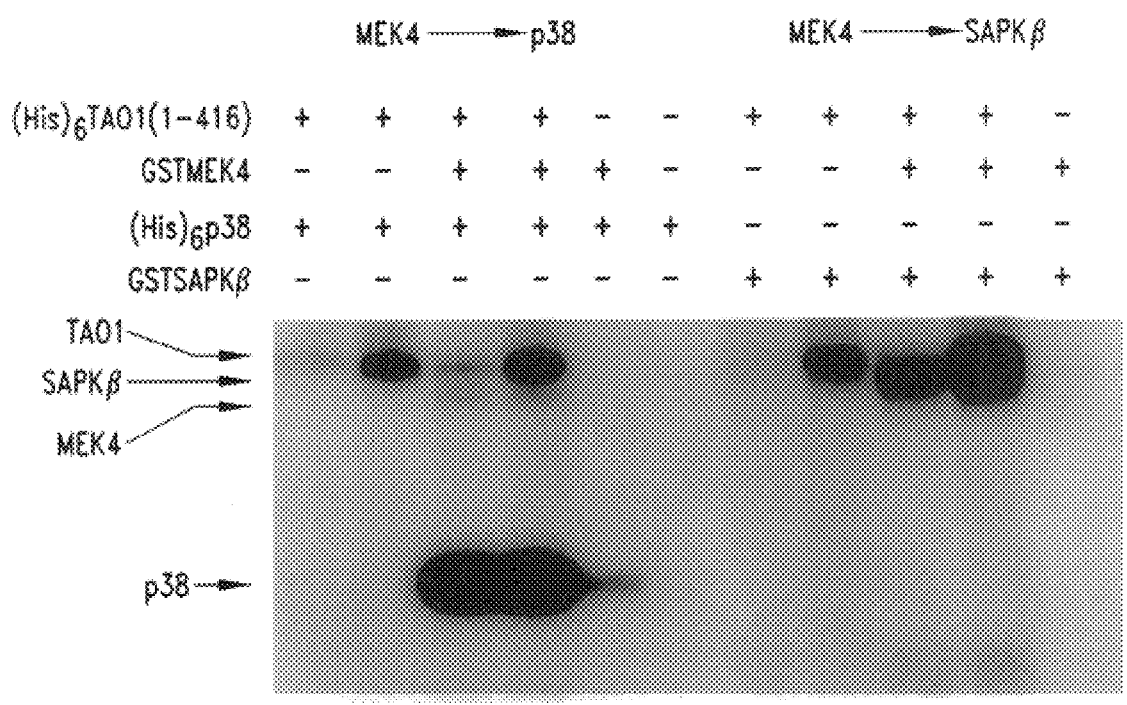
FIG. 7 is an autoradiogram showing the results of a representative in vitro linked kinase assay to estimate MEK activation by TAO1. Only the second part of the linked assay is shown. The assay was identical to that described in FIG. 6, except that GSTMEK4 was substituted for MEK3, and both (His)$_6$p38 and GSTSAPKP were used as MEK4 substrates.
Figure 8:
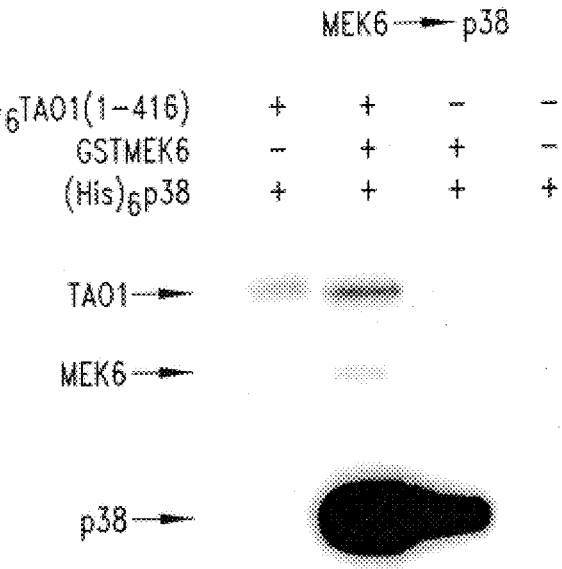
FIG. 8 is an autoradiogram showing the results of a representative in vitro linked kinase assay to estimate MEK activation by TAO1. The assay was as described in FIGS. 6 and 7, but was performed with GSTMEK6 and (His)$_6$p38 as the MEK6 substrate.

(His)$_6$TAO1(1–416) activated GST-MEK4 5-fold toward (His)$_6$p38, and 150-fold towards GST-SAPKβ (FIG. 7). The difference in fold activation seen for MEK4 towards the two substrates probably reflects the difference in basal kinase activity of MEK4 towards p38 and SAPKβ in vitro. TAO1 also increased the ability of GST-MEK6 to phosphorylate (His)$_6$p38, by 5-fold (FIG. 8). Recombinant GST-MEK5 was not phosphorylated by (His)$_6$TAO1(1–416).

Recombinant (His)$_6$TAO1 and (His)$_6$TAO1(D169A) were also examined for their ability to activate the same MEK proteins. (His)$_6$TAO1 showed a reduced ability to activate MEK3 as compared to that of the carboxy-terminal truncation mutant (His)$_6$TAO1(1–416). In multiple experiments, the full-length TAO protein displayed from 0 to 30% of the MEK3 activating ability of (His)$_6$TAO1(1–416), and (His)$_6$TAO1(D169A) was unable to activate any of the MEK proteins above basal activities.

Figure 9:
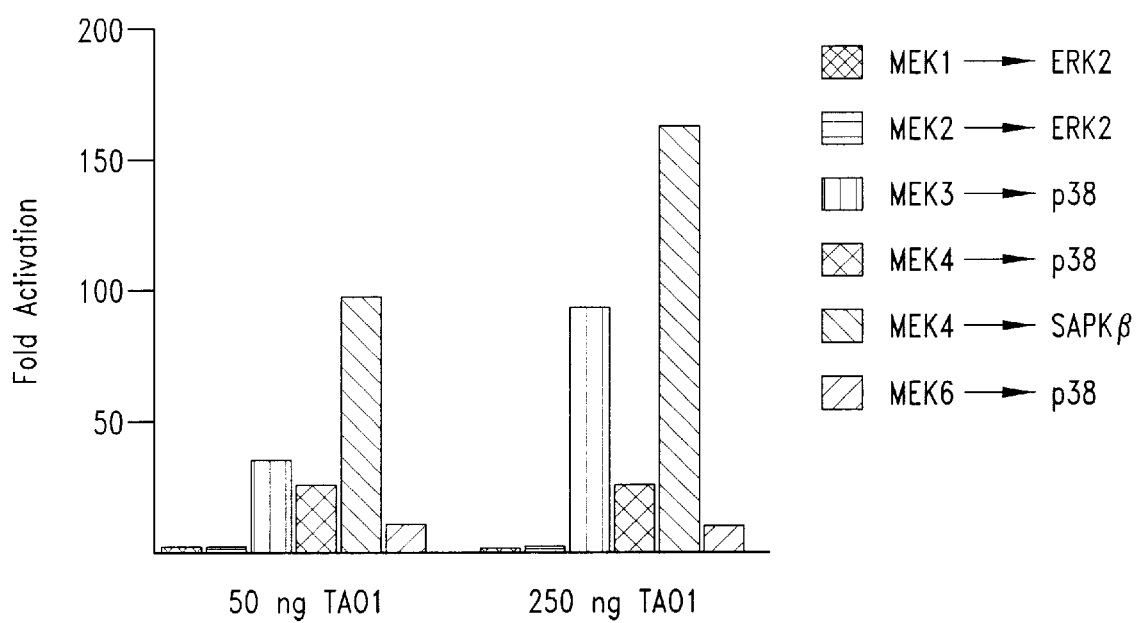
FIG. 9 is a histogram comparing the fold activations of MEKs 1 through 6 by (His)$_6$TAO1(1–416).

The degree of activation of each of the MEK proteins by (His)$_6$TAO1(1–416) in vitro is comparable to that seen by a bacterially produced amino-terminal truncation of MEKK1 (Xu et al., *Proc. Natl. Acad. Sci. USA* 92:6808–6812, 1995; Robinson et al., *J. Biol. Chem.* 271:29734–29739, 1996). To distinguish the MEK-activating ability of TAO1 from that of MEKK, the ability of (His)$_6$TAO1(1–416) to activate MEK1 and MEK2 was assessed. As shown in FIG. 9, (His)$_6$TAO1 (1–416) was completely unable to increase the activity of MEK1 or MEK2 towards the substrate (His)$_6$ERK2 under the same conditions that TAO1 activates MEK3, MEK4, and MEK6. Thus, while TAO1 displays MEKK-like activity in its ability to activate various MEKs, TAO1 is differentiated from MEKK by its inability to recognize MEK1 and MEK2. FIG. 9 shows the fold activation of the various MEKs by TAO1.

Figure 10:
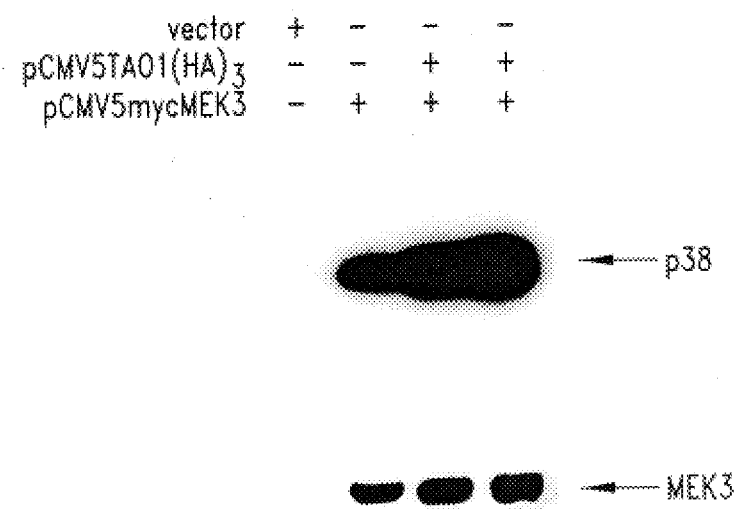
FIG. 10 is an autoradiogram illustrating TAO1 activation of MEK3 in vivo. Human embryonic kidney 293 cells were transiently transfected with either vector alone, or pCMV5TAO1(HA)$_3$ and pCMV5mycMEK3, alone and in combination. Immunoprecipitates made with a monoclonal antibody directed against the myc epitope were subjected to in vitro kinase assays with (His)$_6$p38 as substrate. Myc-tagged MEK3 expression detected with a polyclonal anti-MEK3 antisera is shown below. In several separate experiments, MEK3 activity in the immunoprecipitates was increased 3 to 4 fold when coexpressed with TAO1.

To assess the ability of TAO1 to activate the various MEKs in vivo, full-length HA-tagged TAO1 was co-transfected into 293 cells with myc-tagged MEK3, or myc-tagged TAO1 was co-transfected with HA-tagged MEK4 or HA-tagged MEK6. The pCMV5myc-MEK3 construct was generated by inserting the MEK3 coding sequence (provided by K. L. Guan, University of Michigan, which may be prepared as described by Robinson et al., *J. Biol. Chem.* 271:29734–29739, 1996) into the pCMV5Myc vector, such that the Myc epitope is at the amino-terminus of MEK3. The MEKs were then immunoprecipitated and added to immune complex kinase assays with the appropriate substrate and Mg$^{2+}$/ATP. In multiple experiments, myc-tagged MEK3 showed a 3-fold higher activity toward p38 when immunoprecipitated from 293 cells co-expressing TAO than from cells not transfected with TAO (FIG. 10). In contrast, TAO was not able to increase the activity of immunoprecipitated HA-tagged MEK4 towards GST-SAPKβ, or that of HA-tagged MEK6 toward p38.

In transfected cells, TAO1 activates MEK3 3-fold, but neither MEK4 nor MEK6. The selectivity in transfected cells may arise from the ability of TAO1 to bind MEK3. The endogenous MEK3 from Sf9 cells copurifies with recombinant TAO1 expressed in the cells. These findings suggest that TAO1 may be an important regulator of the p38 pathway.

Figure 11:
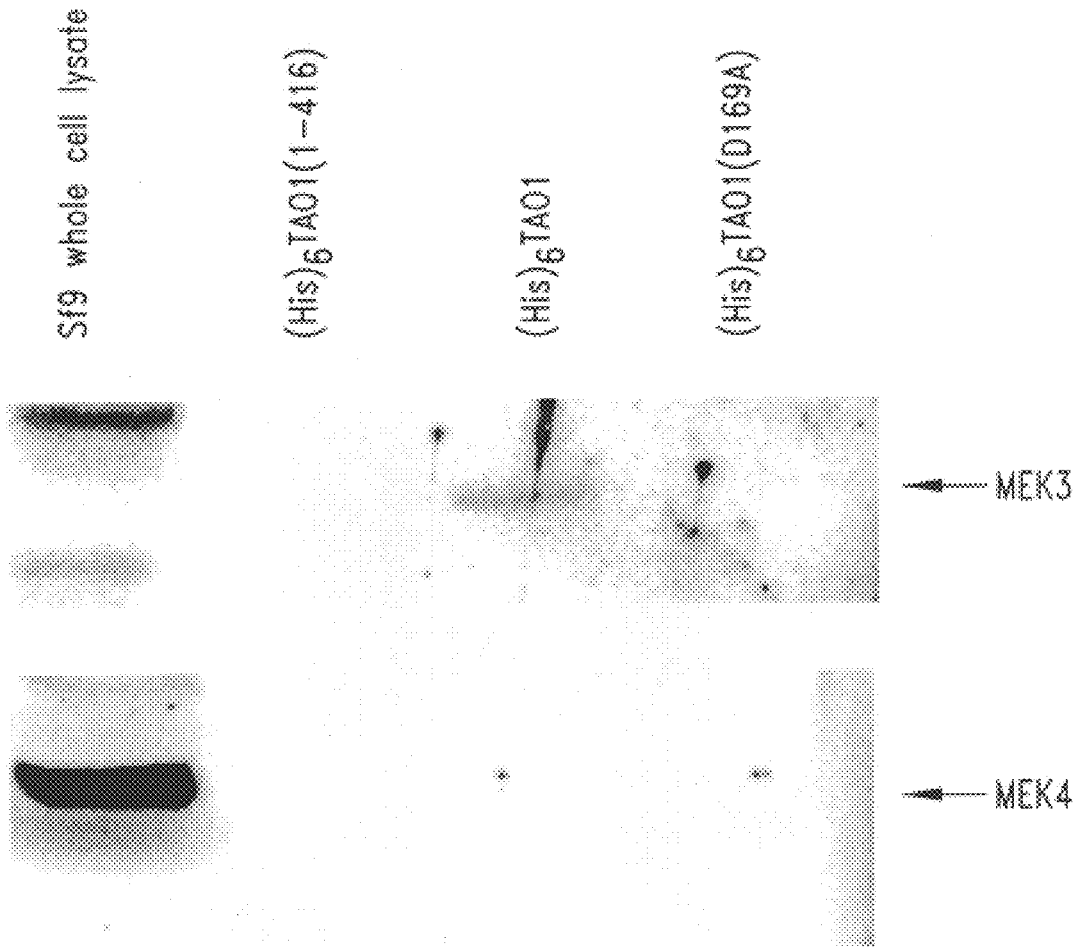
FIG. 11 is an autoradiogram illustrating the copurification of TAO1 and endogenous MEK3 from Sf9 cells. Either 100 μg of Sf9 whole cell lysate, or 1 μg each of the recombinant TAO1 proteins purified from Sf9 cells was Western blotted with polyclonal antisera directed against MEK3 (top panel) or MEK4 (lower panel). An identical Western blot performed with an antisera against MEK6 did not detect MEK6 protein in either the Sf9 lysate or the TAO1 preparations.

To determine which MEK3 residues are phosphorylated by TAO, an in vitro kinase reaction was performed with (His)$_6$TAO1(1–416) and (His)$_6$MEK3; the 57 kDa band corresponding to TAO1 and the 30 kDa band corresponding to MEK3 were excised and treated as described. Phosphoproteins were separated by SDS-PAGE, transferred to Immobilon-P membrane (Millipore) electrophoretically, and visualized by autoradiography. Bands of interest were excised and hydrolyzed in 6M HCl for 60 minutes at 110° C. The hydrolysate was dried under vacuum, and resuspended in a 2.2% formic acid, 12% acetic acid solution at an activity of 2000 cpm/µl. Then 1 µl of each sample was mixed with 1 µg each of the three phosphoamino acid standards, and spotted onto cellulose thin-layer chromatography plates. Electrophoresis was performed in 0.5% pyridine, 5% acetic acid at 1200 volts for 60 minutes. After air drying the plates, the standards were visualized with 0.25% ninhydrin in acetone. Autoradiography revealed only phosphoserine and phosphothreonine in both $(His)_6TAO1$ (1–416) and $(His)_6$ MEK3 (FIG. 11).

Example 4

Co-Purification of MEK3 and TAO1

This Example shows that TAO1 and MEK3 co-purify.

Although the ability of $(His)_6TAO1$ to activate MEK3 was always reduced in comparison with that of $(His)_6TAO1$ (1–416), several assays showed that the ability of $(His)_6TAO1$ to lead to an increase in the phosphorylation of p38 in the linked kinase assays was partly independent of the addition of MEK. $(His)_6TAO1(1–416)$ does not phosphorylate p38. Therefore, Western analyses were performed to determine if one or more MEKs might be present in the TAO1 preparations purified from Sf9 cells.

$(His)_6TAO1$, $(His)_6TAO1(1–416)$, and $(His)_6TAO1$ (D169A) were subjected to Western analysis with antisera specific to MEK3, MEK4, and MEK6. Four different polyclonal antisera were raised to these three TAO1 peptides in rabbits. The peptide TKDAVRELDNLQYRKMKKLL (SEQ ID NO:23) corresponding to the amino acids 296 to 315 yielded antisera P820. The peptide KKELNSFLESQKREYKLRK (SEQ ID NO:24) of amino acids 545 to 563 yielded the antiserum R562. Finally, the peptide RELRELEQRVSLRRALLEQK (SEQ ID NO:25) of amino acids 829 to 848 resulted in the antisera R564 and R565. These peptides were conjugated to Limulus hemocyanin (Boulton and Cobb, Cell. Regul. 2:357–371, 1991) and dialyzed into phosphate-buffered saline. A total of five boosts were performed, after which the rabbits were exsanguinated and the serum collected. The antisera were screened for reactivity by Western blotting of recombinant TAO1 expressed in Sf9 cells. Five antisera were found to consistently recognize the recombinant TAO1 protein in Western blots. Free peptide was able to block the specific recognition of TAO1 protein by the antisera. None of the five antisera detected the presence of TAO1 in lysates of 293, NIH3T3, NG-108, or COS cells.

For immunoblot analysis, either 50 ng of recombinant TAO1 protein or 100 µg of cell lysate was subjected to SDS-PAGE, then transferred to nitrocellulose membranes. The membranes were blocked with 5% nonfat powdered milk in TBST (20 mM Tris, pH 8, 500 mM NaCl, 0.05% Tween 20) for one hour, then incubated with the polyclonal antisera at 1:500 dilution in TBST plus 0.25% milk for one hour. After three washes with TBST, the membranes were incubated with a 1:2500 dilution of horseradish peroxidase-conjugated goat-anti-rabbit IgG in TBST plus 0.25% milk for one hour. Membranes were washed again in TBST then visualized with the ECL system (Amersham).

MEK3 was clearly seen in the $(His)_6TAO1$ preparation, and to a lesser extent in the $(His)_6TAO1(D169A)$ preparation (FIG. 11). MEK4 was detected in the Sf9 cell lysates, but not in the TAO1 preparations, while MEK6 was detected in neither.

From the foregoing, it will be appreciated that, although specific embodiments of the invention have been described herein for the purpose of illustration, various modifications may be made without deviating from the spirit and scope of the invention.

What is claimed is:

1. An isolated polypeptide comprising an amino acid sequence provided in SEQ ID NO:2, or a variant thereof that is at least 80% identical to SEQ ID NO:2 and that differs from SEQ ID NO:2 only in one or more amino acid substitutions, additions of terminal amino acid residues and/or deletions of terminal amino acid residues, wherein the ability of the variant to phosphorylate MEK3 is not substantially diminished.

2. A polypeptide according to claim 1, wherein the polypeptide comprises a sequence that differs from a sequence recited in SEQ ID NO:2 only in conservative substitutions, such that the polypeptide is at least 90% identical to SEQ ID NO:2.

3. A polypeptide according to claim 1, wherein the polypeptide comprises amino acids 1–416 of SEQ ID NO:2.

4. An isolated polypeptide comprising an amino acid sequence provided in SEQ ID NO:2 modified such that aspartic acid residue 169 is replaced with alanine.

5. An isolated polypeptide comprising an amino acid sequence provided in SEQ ID NO:4, or a variant thereof that is at least 80% identical to SEQ ID NO:4 and that differs from SEQ ID NO:4 only in one or more amino acid substitutions, additions of terminal amino acid residues and/or deletions of terminal amino acid residues, wherein the ability of the variant to phosphorylate MEK3 is not substantially diminished.

6. A polypeptide according to claim 5, wherein the polypeptide comprises a sequence that differs from a sequence recited in SEQ ID NO:4 only in conservative substitutions, such that the polypeptide is at least 90% identical to SEQ ID NO:4.

7. A polypeptide according to claim 5, which is constitutively active.

8. A pharmaeutical composition, comprising:

(a) a polypeptide according to any one of claims 1–7; and (b) a physiologically acceptable carrier.

* * * * *

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
        (A) LENGTH: 3312 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 121..3123

(xi) SEQUENCE DESCRIPTION: SEQ ID NO: 1:

```
TCTGCAGTAT GGTAGATTAT TATTTATGCA TTTATGCCAG TGTGGCTTCA TTCATACAGA         60

TGAACCAAGC TTTGGGATAG CAGTATAAAA TTAGAATCAG ACAGCTGACT GCTCAGCAGG        120

ATG CCA TCA ACT AAC AGA GCA GGC AGT CTA AAG GAC CCT GAA ATC GCA          168
Met Pro Ser Thr Asn Arg Ala Gly Ser Leu Lys Asp Pro Glu Ile Ala
  1               5                  10                  15

GAG CTC TTC TTC AAA GAA GAT CCG GAA AAA CTC TTC ACA GAT CTC AGA          216
```

```
                                            -continued

Glu Leu Phe Phe Lys Glu Asp Pro Glu Lys Leu Phe Thr Asp Leu Arg
             20                  25                  30

GAA ATC GGC CAT GGG AGC TTT GGA GCA GTT TAT TTT GCA CGA GAT GTG    264
Glu Ile Gly His Gly Ser Phe Gly Ala Val Tyr Phe Ala Arg Asp Val
         35                  40                  45

CGT ACT AAT GAA GTG GTG GCC ATC AAG AAA ATG TCT TAT AGT GGA AAG    312
Arg Thr Asn Glu Val Val Ala Ile Lys Lys Met Ser Tyr Ser Gly Lys
 50                  55                  60

CAG TCT ACT GAG AAA TGG CAG GAT ATT ATT AAG GAA GTC AAG TTT CTA    360
Gln Ser Thr Glu Lys Trp Gln Asp Ile Ile Lys Glu Val Lys Phe Leu
 65                  70                  75                  80

CAA AGA ATA AAA CAT CCC AAC AGT ATA GAA TAC AAA GGC TGC TAT TTA    408
Gln Arg Ile Lys His Pro Asn Ser Ile Glu Tyr Lys Gly Cys Tyr Leu
                 85                  90                  95

CGT GAA CAC ACA GCA TGG CTT GTA ATG GAA TAT TGT TTA GGA TCT GCT    456
Arg Glu His Thr Ala Trp Leu Val Met Glu Tyr Cys Leu Gly Ser Ala
            100                 105                 110

TCG GAT TTA CTA GAA GTT CAT AAA AAG CCA TTA CAA GAA GTG GAA ATA    504
Ser Asp Leu Leu Glu Val His Lys Lys Pro Leu Gln Glu Val Glu Ile
        115                 120                 125

GCA GCA ATT ACA CAT GGT GCT CTC CAG GGA TTA GCT TAT TTA CAT TCT    552
Ala Ala Ile Thr His Gly Ala Leu Gln Gly Leu Ala Tyr Leu His Ser
    130                 135                 140

CAT ACC ATG ATC CAT AGA GAT ATC AAA GCA GGA AAT ATC CTT CTG ACA    600
His Thr Met Ile His Arg Asp Ile Lys Ala Gly Asn Ile Leu Leu Thr
145                 150                 155                 160

GAA CCA GGC CAA GTG AAA CTT GCT GAC TTT GGA TCT GCT TCC ATG GCC    648
Glu Pro Gly Gln Val Lys Leu Ala Asp Phe Gly Ser Ala Ser Met Ala
                165                 170                 175

TCC CCT GCC AAT TCT TTT GTG GGA ACA CCA TAT TGG ATG GCC CCA GAA    696
Ser Pro Ala Asn Ser Phe Val Gly Thr Pro Tyr Trp Met Ala Pro Glu
            180                 185                 190

GTA ATT TTA GCC ATG GAT GAA GGA CAA TAT GAT GGC AAA GTT GAT GTA    744
Val Ile Leu Ala Met Asp Glu Gly Gln Tyr Asp Gly Lys Val Asp Val
        195                 200                 205

TGG TCT CTT GGA ATA ACA TGT ATT GAA TTA GCC GAG AGG AAG CCT CCT    792
Trp Ser Leu Gly Ile Thr Cys Ile Glu Leu Ala Glu Arg Lys Pro Pro
    210                 215                 220

TTA TTT AAT ATG AAT GCA ATG AGT GCC TTA TAT CAC ATA GCC CAA AAT    840
Leu Phe Asn Met Asn Ala Met Ser Ala Leu Tyr His Ile Ala Gln Asn
225                 230                 235                 240

GAA TCC CCT ACA CTA CAG TCT AAT GAA TGG TCT GAT TAT TTT CGA AAC    888
Glu Ser Pro Thr Leu Gln Ser Asn Glu Trp Ser Asp Tyr Phe Arg Asn
                245                 250                 255

TTT GTA GAT TCT TGC CTC CAG AAA ATC CCT CAA GAT CGC CCT ACA TCA    936
Phe Val Asp Ser Cys Leu Gln Lys Ile Pro Gln Asp Arg Pro Thr Ser
            260                 265                 270

GAG GAA CTT TTA AAG CAC ATG TTT GTT CTT CGA GAG CGC CCT GAA ACA    984
Glu Glu Leu Leu Lys His Met Phe Val Leu Arg Glu Arg Pro Glu Thr
        275                 280                 285

GTG TTA ATA GAT CTT ATT CAA AGG ACA AAG GAT GCA GTA AGA GAG CTG   1032
Val Leu Ile Asp Leu Ile Gln Arg Thr Lys Asp Ala Val Arg Glu Leu
    290                 295                 300

GAC AAT CTA CAA TAT CGA AAG ATG AAG AAA CTC CTT TTC CAG GAG GCA   1080
Asp Asn Leu Gln Tyr Arg Lys Met Lys Lys Leu Leu Phe Gln Glu Ala
305                 310                 315                 320

CAT AAT GGA CCA GCA GTA GAA GCA CAG GAA GAA GAG GAG GAA CAA GAT   1128
His Asn Gly Pro Ala Val Glu Ala Gln Glu Glu Glu Glu Glu Gln Asp
                325                 330                 335
```

```
CAT GGT GGT GGC CGG ACA GGA ACA GTA AAT AGT GTT GGA AGC AAT CAG      1176
His Gly Gly Gly Arg Thr Gly Thr Val Asn Ser Val Gly Ser Asn Gln
            340                 345                 350

TCT ATC CCC AGT ATG TCT ATC AGT GCC AGT AGC CAA AGC AGC AGT GTT      1224
Ser Ile Pro Ser Met Ser Ile Ser Ala Ser Ser Gln Ser Ser Ser Val
            355                 360                 365

AAT AGT CTT CCA GAT GCA TCG GAT GAC AAG AGT GAG CTA GAC ATG ATG      1272
Asn Ser Leu Pro Asp Ala Ser Asp Asp Lys Ser Glu Leu Asp Met Met
            370                 375                 380

GAG GGA GAC CAT ACA GTG ATG TCT AAC AGT TCT GTC ATC CAC TTA AAA      1320
Glu Gly Asp His Thr Val Met Ser Asn Ser Ser Val Ile His Leu Lys
385                 390                 395                 400

CCT GAG GAG GAA AAT TAC CAA GAA GAA GGA GAT CCT AGA ACA AGA GCA      1368
Pro Glu Glu Glu Asn Tyr Gln Glu Glu Gly Asp Pro Arg Thr Arg Ala
                405                 410                 415

TCA GCT CCA CAG TCT CCA CCT CAA GTG TCT CGT CAC AAA TCA CAT TAT      1416
Ser Ala Pro Gln Ser Pro Pro Gln Val Ser Arg His Lys Ser His Tyr
            420                 425                 430

CGT AAT AGA GAA CAC TTT GCA ACT ATA CGA ACA GCA TCA CTG GTT ACA      1464
Arg Asn Arg Glu His Phe Ala Thr Ile Arg Thr Ala Ser Leu Val Thr
            435                 440                 445

AGA CAG ATG CAA GAA CAT GAG CAG GAC TCT GAA CTT AGA GAA CAG ATG      1512
Arg Gln Met Gln Glu His Glu Gln Asp Ser Glu Leu Arg Glu Gln Met
450                 455                 460

TCT GGT TAT AAG CGG ATG AGG CGA CAG CAT CAG AAG CAG CTG ATG ACT      1560
Ser Gly Tyr Lys Arg Met Arg Arg Gln His Gln Lys Gln Leu Met Thr
465                 470                 475                 480

CTG GAA AAT AAA CTG AAG GCA GAA ATG GAC GAA CAT CGG CTC AGA TTA      1608
Leu Glu Asn Lys Leu Lys Ala Glu Met Asp Glu His Arg Leu Arg Leu
                485                 490                 495

GAC AAA GAT CTT GAA ACT CAG CGC AAC AAT TTC GCT GCA GAA ATG GAG      1656
Asp Lys Asp Leu Glu Thr Gln Arg Asn Asn Phe Ala Ala Glu Met Glu
            500                 505                 510

AAA CTT ATT AAG AAA CAC CAA GCT TCT ATG GAA AAA GAG GCT AAA GTG      1704
Lys Leu Ile Lys Lys His Gln Ala Ser Met Glu Lys Glu Ala Lys Val
            515                 520                 525

ATG GCC AAC GAG GAG AAA AAA TTC CAA CAA CAC ATT CAG GCT CAA CAG      1752
Met Ala Asn Glu Glu Lys Lys Phe Gln Gln His Ile Gln Ala Gln Gln
530                 535                 540

AAG AAA GAA CTG AAT AGC TTT TTG GAG TCT CAA AAA AGA GAA TAT AAA      1800
Lys Lys Glu Leu Asn Ser Phe Leu Glu Ser Gln Lys Arg Glu Tyr Lys
545                 550                 555                 560

CTT CGA AAA GAG CAG CTT AAG GAG GAG CTG AAT GAA AAC CAG AGC ACA      1848
Leu Arg Lys Glu Gln Leu Lys Glu Glu Leu Asn Glu Asn Gln Ser Thr
                565                 570                 575

CCT AAA AAA GAA AAG CAG GAA TGG CTT TCA AAG CAG AAG GAG AAT ATT      1896
Pro Lys Lys Glu Lys Gln Glu Trp Leu Ser Lys Gln Lys Glu Asn Ile
            580                 585                 590

CAA CAT TTT CAG GCA GAA GAA GAA GCT AAT CTT CTT CGA CGT CAA AGG      1944
Gln His Phe Gln Ala Glu Glu Glu Ala Asn Leu Leu Arg Arg Gln Arg
            595                 600                 605

CAG TAT CTA GAG CTA GAA TGT CGT CGC TTC AAA AGA AGA ATG TTA CTT      1992
Gln Tyr Leu Glu Leu Glu Cys Arg Arg Phe Lys Arg Arg Met Leu Leu
            610                 615                 620

GGT CGG CAT AAC TTG GAA CAG GAC CTT GTC AGG GAG GAG TTA AAC AAA      2040
Gly Arg His Asn Leu Glu Gln Asp Leu Val Arg Glu Glu Leu Asn Lys
625                 630                 635                 640

AGG CAG ACT CAG AAG GAC TTA GAA CAT GCA ATG TTA CTG CGA CAG CAT      2088
Arg Gln Thr Gln Lys Asp Leu Glu His Ala Met Leu Leu Arg Gln His
                645                 650                 655
```

```
GAA TCC ATG CAA GAA CTG GAG TTT CGC CAC CTC AAC ACT ATT CAG AAG      2136
Glu Ser Met Gln Glu Leu Glu Phe Arg His Leu Asn Thr Ile Gln Lys
            660                 665                 670

ATG CGC TGT GAG TTG ATC AGA CTG CAA CAT CAA ACT GAG CTT ACT AAC      2184
Met Arg Cys Glu Leu Ile Arg Leu Gln His Gln Thr Glu Leu Thr Asn
            675                 680                 685

CAG CTG GAA TAC AAT AAG AGA AGG GAA CGG GAA CTA AGA CGG AAA CAT      2232
Gln Leu Glu Tyr Asn Lys Arg Arg Glu Arg Glu Leu Arg Arg Lys His
        690                 695                 700

GTC ATG GAA GTT CGA CAG CAG CCT AAG AGT TTG AAG TCT AAA GAA CTC      2280
Val Met Glu Val Arg Gln Gln Pro Lys Ser Leu Lys Ser Lys Glu Leu
705                 710                 715                 720

CAA ATA AAA AAG CAG TTT CAG GAT ACC TGC AAA ATT CAA ACC AGA CAG      2328
Gln Ile Lys Lys Gln Phe Gln Asp Thr Cys Lys Ile Gln Thr Arg Gln
            725                 730                 735

TAC AAA GCA TTA AGG AAT CAC CTA CTG GAG ACT ACA CCA AAG AGT GAG      2376
Tyr Lys Ala Leu Arg Asn His Leu Leu Glu Thr Thr Pro Lys Ser Glu
            740                 745                 750

CAC AAA GCT GTT CTG AAA AGA CTC AAG GAG GAA CAG ACT CGG AAG TTA      2424
His Lys Ala Val Leu Lys Arg Leu Lys Glu Glu Gln Thr Arg Lys Leu
            755                 760                 765

GCC ATC TTG GCT GAG CAG TAT GAT CAT AGC ATT AAT GAA ATG CTC TCC      2472
Ala Ile Leu Ala Glu Gln Tyr Asp His Ser Ile Asn Glu Met Leu Ser
770                 775                 780

ACA CAA GCT CTG CGT TTG GAT GAA GCA CAG GAA GCA GAA TGC CAG GTT      2520
Thr Gln Ala Leu Arg Leu Asp Glu Ala Gln Glu Ala Glu Cys Gln Val
785                 790                 795                 800

TTG AAG ATG CAG CTA CAG CAG GAA CTG GAG CTG TTG AAT GCA TAT CAG      2568
Leu Lys Met Gln Leu Gln Gln Glu Leu Glu Leu Leu Asn Ala Tyr Gln
            805                 810                 815

AGC AAA ATC AAG ATG CAG GCT GAG GCC CAA CAT GAT CGA GAG CTT CGA      2616
Ser Lys Ile Lys Met Gln Ala Glu Ala Gln His Asp Arg Glu Leu Arg
            820                 825                 830

GAG CTG GAA CAA AGG GTC TCC CTT CGG AGA GCA CTC TTA GAA CAG AAG      2664
Glu Leu Glu Gln Arg Val Ser Leu Arg Arg Ala Leu Leu Glu Gln Lys
            835                 840                 845

ATT GAA GAA GAG ATG TTG GCT TTG CAG AAT GAA CGC ACA GAA CGA ATA      2712
Ile Glu Glu Glu Met Leu Ala Leu Gln Asn Glu Arg Thr Glu Arg Ile
850                 855                 860

CGT AGC CTG CTC GAG CGC CAG GCC AGA GAA ATT GAA GCT TTT GAC TCT      2760
Arg Ser Leu Leu Glu Arg Gln Ala Arg Glu Ile Glu Ala Phe Asp Ser
865                 870                 875                 880

GAA AGC ATG AGA TTA GGT TTT AGT AAC ATG GTC CTT TCT AAT CTC TCC      2808
Glu Ser Met Arg Leu Gly Phe Ser Asn Met Val Leu Ser Asn Leu Ser
            885                 890                 895

CCT GAG GCA TTC AGC CAC AGC TAC CCA GGA GCT TCT AGC TGG TCT CAC      2856
Pro Glu Ala Phe Ser His Ser Tyr Pro Gly Ala Ser Ser Trp Ser His
            900                 905                 910

AAT CCT ACT GGG GGT TCA GGA CCT CAC TGG GGT CAT CCC ATG GGT GGC      2904
Asn Pro Thr Gly Gly Ser Gly Pro His Trp Gly His Pro Met Gly Gly
            915                 920                 925

ACA CCA CAA GCT TGG GGT CAT CCG ATG CAA GGC GGA CCC CAA CCA TGG      2952
Thr Pro Gln Ala Trp Gly His Pro Met Gln Gly Gly Pro Gln Pro Trp
            930                 935                 940

GGT CAC CCC TCA GGG CCA ATG CAA GGG GTA CCT CGA GGT AGC AGT ATA      3000
Gly His Pro Ser Gly Pro Met Gln Gly Val Pro Arg Gly Ser Ser Ile
945                 950                 955                 960

GGA GTC CGC AAT AGC CCC CAG GCT CTG AGG CGG ACA GCT TCT GGG GGA      3048
Gly Val Arg Asn Ser Pro Gln Ala Leu Arg Arg Thr Ala Ser Gly Gly
```

```
                    965               970               975
CGG ACG GAA CAG GGC ATG AGC AGA AGC ACG AGT GTC ACT TCA CAA ATA        3096
Arg Thr Glu Gln Gly Met Ser Arg Ser Thr Ser Val Thr Ser Gln Ile
            980                 985                 990

TCC AAT GGG TCA CAC ATG TCT TAC ACA TAATAATTGA AAGTGGCAAT              3143
Ser Asn Gly Ser His Met Ser Tyr Thr
            995                 1000

TCCGCTGGAG CTGTCTGCCA AAAGAAACTG CCTACAGACA TCAGCACAGC AGCCTCCTCA      3203

CTTGGGTACT ACCGGGTGGA AGCTGTGCAT ATGGTATATT TTATTCGTCT TTGTAAAGCG      3263

TTATGTTTTG TGTTTACTAA TTGGGATGTC ATAGTATTTG GCTGCCGGG                  3312

(2) INFORMATION FOR SEQ ID NO: 2:

(i) SEQUENCE CHARACTERISTICS:
        (A) LENGTH: 1001 amino acids
        (B) TYPE: amino acid
        (D) TOPOLOGY: linear (ii) MOLECULE TYPE: protein (xi) SEQUENCE DESCRIPTION: SEQ ID NO: 2:

Met Pro Ser Thr Asn Arg Ala Gly Ser Leu Lys Asp Pro Glu Ile Ala
 1               5                  10                  15

Glu Leu Phe Phe Lys Glu Asp Pro Glu Lys Leu Phe Thr Asp Leu Arg
                20                  25                  30

Glu Ile Gly His Gly Ser Phe Gly Ala Val Tyr Phe Ala Arg Asp Val
            35                  40                  45

Arg Thr Asn Glu Val Val Ala Ile Lys Lys Met Ser Tyr Ser Gly Lys
        50                  55                  60

Gln Ser Thr Glu Lys Trp Gln Asp Ile Ile Lys Glu Val Lys Phe Leu
65                  70                  75                  80

Gln Arg Ile Lys His Pro Asn Ser Ile Glu Tyr Lys Gly Cys Tyr Leu
                85                  90                  95

Arg Glu His Thr Ala Trp Leu Val Met Glu Tyr Cys Leu Gly Ser Ala
            100                 105                 110

Ser Asp Leu Leu Glu Val His Lys Lys Pro Leu Gln Glu Val Glu Ile
        115                 120                 125

Ala Ala Ile Thr His Gly Ala Leu Gln Gly Leu Ala Tyr Leu His Ser
    130                 135                 140

His Thr Met Ile His Arg Asp Ile Lys Ala Gly Asn Ile Leu Leu Thr
145                 150                 155                 160

Glu Pro Gly Gln Val Lys Leu Ala Asp Phe Gly Ser Ala Ser Met Ala
                165                 170                 175

Ser Pro Ala Asn Ser Phe Val Gly Thr Pro Tyr Trp Met Ala Pro Glu
            180                 185                 190

Val Ile Leu Ala Met Asp Glu Gly Gln Tyr Asp Gly Lys Val Asp Val
        195                 200                 205

Trp Ser Leu Gly Ile Thr Cys Ile Glu Leu Ala Glu Arg Lys Pro Pro
    210                 215                 220

Leu Phe Asn Met Asn Ala Met Ser Ala Leu Tyr His Ile Ala Gln Asn
225                 230                 235                 240

Glu Ser Pro Thr Leu Gln Ser Asn Glu Trp Ser Asp Tyr Phe Arg Asn
                245                 250                 255

Phe Val Asp Ser Cys Leu Gln Lys Ile Pro Gln Asp Arg Pro Thr Ser
            260                 265                 270
```

-continued

```
Glu Glu Leu Leu Lys His Met Phe Val Leu Arg Glu Arg Pro Glu Thr
            275                 280                 285

Val Leu Ile Asp Leu Ile Gln Arg Thr Lys Asp Ala Val Arg Glu Leu
    290                 295                 300

Asp Asn Leu Gln Tyr Arg Lys Met Lys Lys Leu Leu Phe Gln Glu Ala
305                 310                 315                 320

His Asn Gly Pro Ala Val Glu Ala Gln Glu Glu Glu Glu Glu Gln Asp
                325                 330                 335

His Gly Gly Gly Arg Thr Gly Thr Val Asn Ser Val Gly Ser Asn Gln
            340                 345                 350

Ser Ile Pro Ser Met Ser Ile Ser Ala Ser Ser Gln Ser Ser Ser Val
        355                 360                 365

Asn Ser Leu Pro Asp Ala Ser Asp Asp Lys Ser Glu Leu Asp Met Met
    370                 375                 380

Glu Gly Asp His Thr Val Met Ser Asn Ser Ser Val Ile His Leu Lys
385                 390                 395                 400

Pro Glu Glu Glu Asn Tyr Gln Glu Gly Asp Pro Arg Thr Arg Ala
                405                 410                 415

Ser Ala Pro Gln Ser Pro Gln Val Ser Arg His Lys Ser His Tyr
            420                 425                 430

Arg Asn Arg Glu His Phe Ala Thr Ile Arg Thr Ala Ser Leu Val Thr
            435                 440                 445

Arg Gln Met Gln Glu His Glu Gln Asp Ser Glu Leu Arg Glu Gln Met
450                 455                 460

Ser Gly Tyr Lys Arg Met Arg Arg Gln His Gln Lys Gln Leu Met Thr
465                 470                 475                 480

Leu Glu Asn Lys Leu Lys Ala Glu Met Asp Glu His Arg Leu Arg Leu
                485                 490                 495

Asp Lys Asp Leu Glu Thr Gln Arg Asn Asn Phe Ala Ala Glu Met Glu
            500                 505                 510

Lys Leu Ile Lys Lys His Gln Ala Ser Met Glu Lys Glu Ala Lys Val
        515                 520                 525

Met Ala Asn Glu Glu Lys Lys Phe Gln Gln His Ile Gln Ala Gln Gln
530                 535                 540

Lys Lys Glu Leu Asn Ser Phe Leu Glu Ser Gln Lys Arg Glu Tyr Lys
545                 550                 555                 560

Leu Arg Lys Glu Gln Leu Lys Glu Glu Leu Asn Glu Asn Gln Ser Thr
                565                 570                 575

Pro Lys Lys Glu Lys Gln Glu Trp Leu Ser Lys Gln Lys Glu Asn Ile
            580                 585                 590

Gln His Phe Gln Ala Glu Glu Ala Asn Leu Leu Arg Arg Gln Arg
        595                 600                 605

Gln Tyr Leu Glu Leu Glu Cys Arg Arg Phe Lys Arg Arg Met Leu Leu
    610                 615                 620

Gly Arg His Asn Leu Glu Gln Asp Leu Val Arg Glu Glu Leu Asn Lys
625                 630                 635                 640

Arg Gln Thr Gln Lys Asp Leu Glu His Ala Met Leu Leu Arg Gln His
                645                 650                 655

Glu Ser Met Gln Glu Leu Glu Phe Arg His Leu Asn Thr Ile Gln Lys
            660                 665                 670

Met Arg Cys Glu Leu Ile Arg Leu Gln His Gln Thr Glu Leu Thr Asn
        675                 680                 685

Gln Leu Glu Tyr Asn Lys Arg Arg Glu Arg Glu Leu Arg Arg Lys His
```

|                     |                     |                     |
|---------------------|---------------------|---------------------|
| 690                 | 695                 | 700                 |

Val Met Glu Val Arg Gln Gln Pro Lys Ser Leu Lys Ser Lys Glu Leu
705                 710                 715                 720

Gln Ile Lys Lys Gln Phe Gln Asp Thr Cys Lys Ile Gln Thr Arg Gln
                725                 730                 735

Tyr Lys Ala Leu Arg Asn His Leu Leu Glu Thr Thr Pro Lys Ser Glu
                740                 745                 750

His Lys Ala Val Leu Lys Arg Leu Lys Glu Glu Gln Thr Arg Lys Leu
                755                 760                 765

Ala Ile Leu Ala Glu Gln Tyr Asp His Ser Ile Asn Glu Met Leu Ser
770                 775                 780

Thr Gln Ala Leu Arg Leu Asp Glu Ala Gln Glu Ala Glu Cys Gln Val
785                 790                 795                 800

Leu Lys Met Gln Leu Gln Gln Glu Leu Glu Leu Leu Asn Ala Tyr Gln
                805                 810                 815

Ser Lys Ile Lys Met Gln Ala Glu Ala Gln His Asp Arg Glu Leu Arg
                820                 825                 830

Glu Leu Glu Gln Arg Val Ser Leu Arg Arg Ala Leu Leu Glu Gln Lys
                835                 840                 845

Ile Glu Glu Glu Met Leu Ala Leu Gln Asn Glu Arg Thr Glu Arg Ile
850                 855                 860

Arg Ser Leu Leu Glu Arg Gln Ala Arg Glu Ile Glu Ala Phe Asp Ser
865                 870                 875                 880

Glu Ser Met Arg Leu Gly Phe Ser Asn Met Val Leu Ser Asn Leu Ser
                885                 890                 895

Pro Glu Ala Phe Ser His Ser Tyr Pro Gly Ala Ser Ser Trp Ser His
                900                 905                 910

Asn Pro Thr Gly Gly Ser Gly Pro His Trp Gly His Pro Met Gly Gly
                915                 920                 925

Thr Pro Gln Ala Trp Gly His Pro Met Gln Gly Gly Pro Gln Pro Trp
                930                 935                 940

Gly His Pro Ser Gly Pro Met Gln Gly Val Pro Arg Gly Ser Ser Ile
945                 950                 955                 960

Gly Val Arg Asn Ser Pro Gln Ala Leu Arg Arg Thr Ala Ser Gly Gly
                965                 970                 975

Arg Thr Glu Gln Gly Met Ser Arg Ser Thr Ser Val Thr Ser Gln Ile
                980                 985                 990

Ser Asn Gly Ser His Met Ser Tyr Thr
                995                 1000

(2) INFORMATION FOR SEQ ID NO: 3:

(i) SEQUENCE CHARACTERISTICS:
        (A) LENGTH: 4296 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 193..3171

(xi) SEQUENCE DESCRIPTION: SEQ ID NO: 3:

| | | | | |
|---|---|---|---|---|
| AGGGGAGGCT | TCCCGGGCCC | GCCCCTCAGG | AAGGGCGAAA | GCTGAGGAAG AGGTGGCGAG | 60 |
| GGGGAAGGTC | TCCTTGCCCC | TCTCCCCGCT | TGTCAGAGCA | ACTGGAGTAC CCCAGGCGGA | 120 |
| AGCGGAGGCG | CTGGGGCACC | ATAGTGACCC | CTACCAGGCA | AGATCCCAAT TTCAGGGCCC | 180 |

```
CCAGGGGCCA TC ATG CCA GCT GGG GGC CGG GCC GGG AGC CTG AAG GAC         228
              Met Pro Ala Gly Gly Arg Ala Gly Ser Leu Lys Asp
                1           5                  10

CCT GAT GTA GCT GAG CTC TTC TTC AAA GAT GAC CCT GAG AAG CTT TTC       276
Pro Asp Val Ala Glu Leu Phe Phe Lys Asp Asp Pro Glu Lys Leu Phe
            15                  20                  25

TCT GAC CTC CGG GAA ATT GGC CAT GGC AGT TTT GGA GCT GTG TAC TTT       324
Ser Asp Leu Arg Glu Ile Gly His Gly Ser Phe Gly Ala Val Tyr Phe
        30                  35                  40

GCC CGG GAT GTC CGG AAC AGT GAG GTG GTG GCC ATC AAG AAG ATG TCC       372
Ala Arg Asp Val Arg Asn Ser Glu Val Val Ala Ile Lys Lys Met Ser
    45                  50                  55                  60

TAT AGT GGG AAG CAA TCA AAT GAG AAA TGG CAG GAT ATC ATC AAG GAG       420
Tyr Ser Gly Lys Gln Ser Asn Glu Lys Trp Gln Asp Ile Ile Lys Glu
                65                  70                  75

GTG CGG TTC TTA CAG AAG CTA CGG CAT CCT AAT ACC ATT CAG TAC CGG       468
Val Arg Phe Leu Gln Lys Leu Arg His Pro Asn Thr Ile Gln Tyr Arg
            80                  85                  90

GGC TGT TAC CTG AGG GAG CAC ACA GCT TGG CTG GTG ATG GAG TAT TGC       516
Gly Cys Tyr Leu Arg Glu His Thr Ala Trp Leu Val Met Glu Tyr Cys
        95                  100                 105

CTG GGT TCA GCT TCT GAT CTT CTC GAA GTG CAC AAG AAG CCG CTG CAG       564
Leu Gly Ser Ala Ser Asp Leu Leu Glu Val His Lys Lys Pro Leu Gln
    110                 115                 120

GAG GTA GAG ATT GCA GCT GTG ACC CAT GGT GCG CTT CAG GGC CTG GCC       612
Glu Val Glu Ile Ala Ala Val Thr His Gly Ala Leu Gln Gly Leu Ala
125                 130                 135                 140

TAT CTA CAT TCA CAC AAC ATG ATC CAT AGA GAT GTG AAG GCT GGG AAC       660
Tyr Leu His Ser His Asn Met Ile His Arg Asp Val Lys Ala Gly Asn
                145                 150                 155

ATC TTG CTG TCA GAA CCA GGC TTG GTG AAA CTG GGG GAC TTT GGC TCC       708
Ile Leu Leu Ser Glu Pro Gly Leu Val Lys Leu Gly Asp Phe Gly Ser
            160                 165                 170

GCA TCC ATC ATG GCA CCT GCC AAC TCA TTT GTG GGC ACT CCA TAC TGG       756
Ala Ser Ile Met Ala Pro Ala Asn Ser Phe Val Gly Thr Pro Tyr Trp
        175                 180                 185

ATG GCT CCA GAG GTG ATC CTA GCC ATG GAT GAG GGA CAA TAT GAT GGC       804
Met Ala Pro Glu Val Ile Leu Ala Met Asp Glu Gly Gln Tyr Asp Gly
    190                 195                 200

AAA GTG GAT GTC TGG TCC TTG GGG ATA ACC TGT ATT GAG CTA GCG GAG       852
Lys Val Asp Val Trp Ser Leu Gly Ile Thr Cys Ile Glu Leu Ala Glu
205                 210                 215                 220

CGG AAG CCA CCA CTG TTT AAC ATG AAT GCA ATG AGT GCC TTA TAC CAC       900
Arg Lys Pro Pro Leu Phe Asn Met Asn Ala Met Ser Ala Leu Tyr His
                225                 230                 235

ATT GCA CAG AAT GAA TCC CCT GCT CTC CAG TCA GGA CAC TGG TCT GAG       948
Ile Ala Gln Asn Glu Ser Pro Ala Leu Gln Ser Gly His Trp Ser Glu
            240                 245                 250

TAC TTC CGG AAT TTT GTT GAC TCC TGT CTT CAG AAA ATC CCT CAA GAC       996
Tyr Phe Arg Asn Phe Val Asp Ser Cys Leu Gln Lys Ile Pro Gln Asp
        255                 260                 265

AGA CCA ACC TCA GAG GTT CTT TTG AAG CAC CGC TTT GTG CTC CGG GAG      1044
Arg Pro Thr Ser Glu Val Leu Leu Lys His Arg Phe Val Leu Arg Glu
    270                 275                 280

CGG CCA CCC ACA GTC ATC ATG GAC CTA ATT CAG AGG ACC AAG GAT GCT      1092
Arg Pro Pro Thr Val Ile Met Asp Leu Ile Gln Arg Thr Lys Asp Ala
285                 290                 295                 300

GTA CGG GAA CTA GAT AAC CTG CAG TAC CGA AAG ATG AAG AAG ATA CTA      1140
Val Arg Glu Leu Asp Asn Leu Gln Tyr Arg Lys Met Lys Lys Ile Leu
```

-continued

|  |  |  |  |  |  |  |  |  |  |  |  |  |  |  |  |
|---|---|---|---|---|---|---|---|---|---|---|---|---|---|---|---|
|  |  |  | 305 |  |  |  | 310 |  |  |  |  | 315 |  |  |  |

```
TTC CAA GAG GCA CCC AAT GGC CCT GGT GCT GAG GCC CCA GAG GAA GAG        1188
Phe Gln Glu Ala Pro Asn Gly Pro Gly Ala Glu Ala Pro Glu Glu Glu
            320                 325                 330

GAG GAA GCA GAA CCT TAC ATG CAC CGA GCA GGG ACA CTG ACC AGT CTA        1236
Glu Glu Ala Glu Pro Tyr Met His Arg Ala Gly Thr Leu Thr Ser Leu
            335                 340                 345

GAG AGT AGC CAT TCA GTG CCC AGC ATG TCC ATC AGC GCC TCC AGC CAA        1284
Glu Ser Ser His Ser Val Pro Ser Met Ser Ile Ser Ala Ser Ser Gln
350                 355                 360

AGC AGC TCA GTC AAC AGC CTA GCA GAT GCC TCA GAT AAT GAA GAA GAG        1332
Ser Ser Ser Val Asn Ser Leu Ala Asp Ala Ser Asp Asn Glu Glu Glu
365                 370                 375                 380

GAG GAG GAG GAA GAG GAA GAA GAG GAG GAG GAA GAA GAA GGC CCT            1380
Glu Glu Glu Glu Glu Glu Glu Glu Glu Glu Glu Glu Glu Gly Pro
                385                 390                 395

GAA TCC CGA GAG ATG GCC ATG ATG CAG GAG GGG GAG CAT ACA GTC ACT        1428
Glu Ser Arg Glu Met Ala Met Met Gln Glu Gly Glu His Thr Val Thr
            400                 405                 410

TCC CAC AGC TCC ATC ATC CAC CGG CTG CCG GGC TCA GAC AAC CTA TAT        1476
Ser His Ser Ser Ile Ile His Arg Leu Pro Gly Ser Asp Asn Leu Tyr
            415                 420                 425

GAT GAT CCC TAC CAG CCA GAG ATG ACC CCA GGT CCA CTC CAA CCA CCT        1524
Asp Asp Pro Tyr Gln Pro Glu Met Thr Pro Gly Pro Leu Gln Pro Pro
430                 435                 440

GCA GCC CCT CCC ACC TCC ACC TCC TCC TCT TCT GCT CGC CGC AGA GCT        1572
Ala Ala Pro Pro Thr Ser Thr Ser Ser Ser Ser Ala Arg Arg Arg Ala
445                 450                 455                 460

TAT TGC CGC AAC CGA GAC CAC TTT GCC ACC ATC CGT ACT GCC TCC CTG        1620
Tyr Cys Arg Asn Arg Asp His Phe Ala Thr Ile Arg Thr Ala Ser Leu
            465                 470                 475

GTC AGC CGT CAG ATC CAG GAG CAT GAG CAG GAC TCG GCC CTG CGG GAG        1668
Val Ser Arg Gln Ile Gln Glu His Glu Gln Asp Ser Ala Leu Arg Glu
            480                 485                 490

CAA CTA AGT GGC TAC AAG CGG ATG CGG CGT CAG CAC CAG AAG CAA CTG        1716
Gln Leu Ser Gly Tyr Lys Arg Met Arg Arg Gln His Gln Lys Gln Leu
            495                 500                 505

CTG GCC CTG GAG TCC CGT CTG AGG GGT GAA CGT GAG GAG CAC AGT GGG        1764
Leu Ala Leu Glu Ser Arg Leu Arg Gly Glu Arg Glu Glu His Ser Gly
            510                 515                 520

CGG TTG CAG CGT GAA CTC GAG GCA CAG CGG GCT GGC TTT GGG ACT GAG        1812
Arg Leu Gln Arg Glu Leu Glu Ala Gln Arg Ala Gly Phe Gly Thr Glu
525                 530                 535                 540

GCT GAG AAG CTG GCC CGG AGG CAC CAG GCC ATT GGT GAG AAG GAA GCA        1860
Ala Glu Lys Leu Ala Arg Arg His Gln Ala Ile Gly Glu Lys Glu Ala
            545                 550                 555

CGA GCT GCT CAG GCT GAG GAG CGG AAG TTC CAG CAG CAC ATC TTG GGG        1908
Arg Ala Ala Gln Ala Glu Glu Arg Lys Phe Gln Gln His Ile Leu Gly
            560                 565                 570

CAG CAG AAG AAG GAA CTG GCT GCC CTG CTG GAG GCA CAG AAG CGA ACC        1956
Gln Gln Lys Lys Glu Leu Ala Ala Leu Leu Glu Ala Gln Lys Arg Thr
            575                 580                 585

TAT AAG CTT CGG AAG GAG CAG TTG AAA GAG GAG CTC CAG GAG AAC CCT        2004
Tyr Lys Leu Arg Lys Glu Gln Leu Lys Glu Glu Leu Gln Glu Asn Pro
            590                 595                 600

AGC ACA CCC AAA CGA GAG AAG GCT GAG TGG CTG TTG AGG CAG AAA GAG        2052
Ser Thr Pro Lys Arg Glu Lys Ala Glu Trp Leu Leu Arg Gln Lys Glu
605                 610                 615                 620

CAG TTG CAA CAG TGC CAG GCA GAG GAG GAG GCA GGG CTA CTG CGG AGG        2100
```

```
                                                              -continued

Gln Leu Gln Gln Cys Gln Ala Glu Glu Ala Gly Leu Leu Arg Arg
            625                 630                 635

CAA CGC CAG TAC TTT GAG CTT CAG TGT CGC CAA TAC AAG CGC AAG ATG      2148
Gln Arg Gln Tyr Phe Glu Leu Gln Cys Arg Gln Tyr Lys Arg Lys Met
            640                 645                 650

CTA CTG GCT CGG CAC AGC CTA GAC CAG GAC CTG CTT CGA GAG GAC TTG      2196
Leu Leu Ala Arg His Ser Leu Asp Gln Asp Leu Leu Arg Glu Asp Leu
            655                 660                 665

AAT AAG AAA CAG ACA CAG AAG GAC TTG GAG TGT GCT CTG CTG TTA CGG      2244
Asn Lys Lys Gln Thr Gln Lys Asp Leu Glu Cys Ala Leu Leu Leu Arg
670                 675                 680

CAG CAT GAG GCT ACC CGA GAG CTG GAG CTA CGA CAG CTC CAG GCT GTC      2292
Gln His Glu Ala Thr Arg Glu Leu Glu Leu Arg Gln Leu Gln Ala Val
685                 690                 695                 700

CAG CGC ACA CGT GCT GAA CTC ACC CGC CTT CAG CAC CAG ACA GAG CTA      2340
Gln Arg Thr Arg Ala Glu Leu Thr Arg Leu Gln His Gln Thr Glu Leu
                705                 710                 715

GGC AAC CAG TTG GAG TAC AAC AAG CGA CGG GAG CAA GAG TTG CGG CAG      2388
Gly Asn Gln Leu Glu Tyr Asn Lys Arg Arg Glu Gln Glu Leu Arg Gln
            720                 725                 730

AAG CAC GCG GCC CAG GTT CGC CAG CAG CCC AAG AGC CTC AAA GTA CGT      2436
Lys His Ala Ala Gln Val Arg Gln Gln Pro Lys Ser Leu Lys Val Arg
            735                 740                 745

GCA GGC CAG CTA CCC ATG GGC CTC CCT GCT ACC GGG GCT CTG GGA CCA      2484
Ala Gly Gln Leu Pro Met Gly Leu Pro Ala Thr Gly Ala Leu Gly Pro
750                 755                 760

CTC AGC ACA GGC ACC CTT AGT GAA GAG CAG CCC TGC TCA TCT GGC CAG      2532
Leu Ser Thr Gly Thr Leu Ser Glu Glu Gln Pro Cys Ser Ser Gly Gln
765                 770                 775                 780

GAG GCA ATC CTG GGC CAA AGG ATG CTG GGA GAG GAG GAG GAA GCA GTG      2580
Glu Ala Ile Leu Gly Gln Arg Met Leu Gly Glu Glu Glu Glu Ala Val
                785                 790                 795

CCA GAG AGA ATG ATT CTG GGA AAG GAA GGG ACT ACT TTG GAG CCA GAG      2628
Pro Glu Arg Met Ile Leu Gly Lys Glu Gly Thr Thr Leu Glu Pro Glu
            800                 805                 810

GAG CAG AGG ATT CTG GGG GAA GAA ATG GGA ACC TTT AGT TCC AGC CCA      2676
Glu Gln Arg Ile Leu Gly Glu Glu Met Gly Thr Phe Ser Ser Ser Pro
            815                 820                 825

CAA AAA CAT AGG AGT CTG GTT AAT GAG GAA GAT TGG GAT ATA TCT AAA      2724
Gln Lys His Arg Ser Leu Val Asn Glu Glu Asp Trp Asp Ile Ser Lys
            830                 835                 840

GAA ATG AAG GAG AGT AGA GTC CCA TCC CTG GCA TCC CAG GAG AGA AAT      2772
Glu Met Lys Glu Ser Arg Val Pro Ser Leu Ala Ser Gln Glu Arg Asn
845                 850                 855                 860

ATT ATT GGC CAG GAA GAG GCT GGG GCA TGG AAT CTG TGG GAG AAG GAG      2820
Ile Ile Gly Gln Glu Glu Ala Gly Ala Trp Asn Leu Trp Glu Lys Glu
                865                 870                 875

CAT GGA AAC CTT GTG GAT ATG GAG TTC AAG CTT GGC TGG GTC CAG GGT      2868
His Gly Asn Leu Val Asp Met Glu Phe Lys Leu Gly Trp Val Gln Gly
            880                 885                 890

CCA GTT CTG ACT CCA GTG CCT GAG GAG GAA GAG GAG GAA GAG GAG          2916
Pro Val Leu Thr Pro Val Pro Glu Glu Glu Glu Glu Glu Glu Glu
            895                 900                 905

GGA GGG GCT CCA ATT GGA ACC CCC AGG GAC CCT GGA GAT GGC TGT CCT      2964
Gly Gly Ala Pro Ile Gly Thr Pro Arg Asp Pro Gly Asp Gly Cys Pro
            910                 915                 920

TCC CCA GAT ATC CCC CCA GAG CCA CCT CCA TCA CAT CTG AGA CAG TAC      3012
Ser Pro Asp Ile Pro Pro Glu Pro Pro Pro Ser His Leu Arg Gln Tyr
925                 930                 935                 940
```

```
CCT GCT AGC CAG CTT CCT GGA TTC TTG TCT CAT GGC CTC CTG ACT GGC      3060
Pro Ala Ser Gln Leu Pro Gly Phe Leu Ser His Gly Leu Leu Thr Gly
                945                 950                 955

CTC TCC TTT GCA GTG GGG TCC TCC TCT GGC CTC TTG CCC CTA CTA CTT      3108
Leu Ser Phe Ala Val Gly Ser Ser Ser Gly Leu Leu Pro Leu Leu Leu
                960                 965                 970

CTG CTG CTA CTC CCA TTG CTG GCA CCC AGG TGG AGG TGG CTT GCA GGC      3156
Leu Leu Leu Leu Pro Leu Leu Ala Pro Arg Trp Arg Trp Leu Ala Gly
                975                 980                 985

AGC ACT GCT GGC CCT T GAGGTAGGAC TAGTGGGCCT GGGGGCTTCA                3202
Ser Thr Ala Gly Pro
    990

TACCTGTTCC TTTGTACAGC TCTACACCTG CCACCCAGTC TGTTCTTACT CCTGGCTCAG     3262

GGCACTGCAC TGGGGCTGT CCTTAGCCTG AGCTGGCGCA GAGGCCTTAT GGGTGTGCCT      3322

CTGGGCCTTG GGCTGCCTG GCTCCTAGCT TGGCCCAGCC TGGCTTTACC TCTGGCAGCT      3382

ATGGCGGCTG GGGGCAAATG GGTACGGCAG CAAGGCCCCC AGATGCGTCG GGGCATCTCT     3442

CGACTCTGGT TGCGGGTTCT GCTACGCCTG TCACCCATGG TCTTTCGGGC CCTACAGGGC     3502

TGTGCGGCTG TGGGAGACCG GGGGCTGTTT GCCCTGTACC CTAAGACCAA TAAGAATGGT     3562

TTCCGAAGTC GACTGCCTGT CCCTTGGCCC CGTCAGGGAA ATCCTCGCAC TACACAGCAC     3622

CCACTAGCTC TGTTAGCAAG AGTTTGGGCT CTGTGCAAGG GCTGGAACTG GCGCCTAGCA     3682

CGGGCTAGCC ATAGATTAGC TTCTTGTTTG CCCCCCTGGG CTGTTCATAT ACTAGCTAGC     3742

TGGGGCCTGC TTAAGGGTGA AAGGCCCAGT CGGATCCCTC GGCTGCTACC GCGAAGCCAA     3802

CGCCGTCTTG GGCTCTCAGC TTCCCGACAG CTACCACCAG GGACTGTAGC TGGGCGGAGA     3862

TCTCAGACCC GCAGGGCCCT GCCTCCCTGG AGGTAACCAG TTCTAACCCT CCACCCAAAT     3922

TTAGGGCATT GAGCACTTTA TCTCCCATGA CTCAGTAAAG TCTCTCCAGT CCCTTGGCCT     3982

CTCCTCCCCT TCTGACCTTT CTTCCTCAGT ATGTTTCCCC AGGTCCAATC CCAGCCCCAG     4042

ATGTAGATTT CTAGACAGGC AGCCTCCTCT ACTGTGGAGT CCAGAATGAC ACTCTTGTGT     4102

TTTCCCCAGT CCCCTAAGTT ATTGCTGTCC CCTGCTGTGT GTGTGCTCAT CCTCACCCTC     4162

ATCGGCTCAG GCCTGGGGCC AGGGGTGGCA GGGAGGGAAG TCATGGGGGT TTTCCCTCTT     4222

TGATTTTGTT TTTCTGTCTC CCTTCCAACC TGTCCCCTTC CCCTCCACCA AAAGAGAAAA     4282

AAAAAAAAAA AAAA                                                      4296
```

(2) INFORMATION FOR SEQ ID NO: 4:

(i) SEQUENCE CHARACTERISTICS:
        (A) LENGTH: 993 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Pro Ala Gly Gly Arg Ala Gly Ser Leu Lys Asp Pro Asp Val Ala
 1               5                  10                  15

Glu Leu Phe Phe Lys Asp Asp Pro Glu Lys Leu Phe Ser Asp Leu Arg
                20                  25                  30

Glu Ile Gly His Gly Ser Phe Gly Ala Val Tyr Phe Ala Arg Asp Val
            35                  40                  45

Arg Asn Ser Glu Val Val Ala Ile Lys Lys Met Ser Tyr Ser Gly Lys
        50                  55                  60

Gln Ser Asn Glu Lys Trp Gln Asp Ile Ile Lys Glu Val Arg Phe Leu
```

-continued

```
                65                  70                  75                  80
            Gln Lys Leu Arg His Pro Asn Thr Ile Gln Tyr Arg Gly Cys Tyr Leu
                            85                  90                  95
            Arg Glu His Thr Ala Trp Leu Val Met Glu Tyr Cys Leu Gly Ser Ala
                        100                 105                 110
            Ser Asp Leu Leu Glu Val His Lys Lys Pro Leu Gln Glu Val Glu Ile
                    115                 120                 125
            Ala Ala Val Thr His Gly Ala Leu Gln Gly Leu Ala Tyr Leu His Ser
                130                 135                 140
            His Asn Met Ile His Arg Asp Val Lys Ala Gly Asn Ile Leu Leu Ser
            145                 150                 155                 160
            Glu Pro Gly Leu Val Lys Leu Gly Asp Phe Gly Ser Ala Ser Ile Met
                            165                 170                 175
            Ala Pro Ala Asn Ser Phe Val Gly Thr Pro Tyr Trp Met Ala Pro Glu
                        180                 185                 190
            Val Ile Leu Ala Met Asp Glu Gly Gln Tyr Asp Gly Lys Val Asp Val
                    195                 200                 205
            Trp Ser Leu Gly Ile Thr Cys Ile Glu Leu Ala Glu Arg Lys Pro Pro
                210                 215                 220
            Leu Phe Asn Met Asn Ala Met Ser Ala Leu Tyr His Ile Ala Gln Asn
            225                 230                 235                 240
            Glu Ser Pro Ala Leu Gln Ser Gly His Trp Ser Glu Tyr Phe Arg Asn
                            245                 250                 255
            Phe Val Asp Ser Cys Leu Gln Lys Ile Pro Gln Asp Arg Pro Thr Ser
                        260                 265                 270
            Glu Val Leu Leu Lys His Arg Phe Val Leu Arg Glu Arg Pro Pro Thr
                    275                 280                 285
            Val Ile Met Asp Leu Ile Gln Arg Thr Lys Asp Ala Val Arg Glu Leu
                290                 295                 300
            Asp Asn Leu Gln Tyr Arg Lys Met Lys Lys Ile Leu Phe Gln Glu Ala
            305                 310                 315                 320
            Pro Asn Gly Pro Gly Ala Glu Ala Pro Glu Glu Glu Glu Glu Ala Glu
                            325                 330                 335
            Pro Tyr Met His Arg Ala Gly Thr Leu Thr Ser Leu Glu Ser Ser His
                        340                 345                 350
            Ser Val Pro Ser Met Ser Ile Ser Ala Ser Ser Gln Ser Ser Ser Val
                    355                 360                 365
            Asn Ser Leu Ala Asp Ala Ser Asp Asn Glu Glu Glu Glu Glu Glu Glu
                370                 375                 380
            Glu Glu Glu Glu Glu Glu Glu Glu Gly Pro Glu Ser Arg Glu
            385                 390                 395                 400
            Met Ala Met Met Gln Glu Gly Glu His Thr Val Thr Ser His Ser Ser
                            405                 410                 415
            Ile Ile His Arg Leu Pro Gly Ser Asp Asn Leu Tyr Asp Asp Pro Tyr
                        420                 425                 430
            Gln Pro Glu Met Thr Pro Gly Pro Leu Gln Pro Pro Ala Ala Pro Pro
                    435                 440                 445
            Thr Ser Thr Ser Ser Ser Ser Ala Arg Arg Arg Ala Tyr Cys Arg Asn
                450                 455                 460
            Arg Asp His Phe Ala Thr Ile Arg Thr Ala Ser Leu Val Ser Arg Gln
            465                 470                 475                 480
            Ile Gln Glu His Glu Gln Asp Ser Ala Leu Arg Glu Gln Leu Ser Gly
                            485                 490                 495
```

```
Tyr Lys Arg Met Arg Arg Gln His Gln Lys Gln Leu Leu Ala Leu Glu
            500                 505                 510

Ser Arg Leu Arg Gly Glu Arg Glu Glu His Ser Gly Arg Leu Gln Arg
            515                 520                 525

Glu Leu Glu Ala Gln Arg Ala Gly Phe Gly Thr Glu Ala Glu Lys Leu
            530                 535                 540

Ala Arg Arg His Gln Ala Ile Gly Glu Lys Glu Ala Arg Ala Ala Gln
545                 550                 555                 560

Ala Glu Glu Arg Lys Phe Gln Gln His Ile Leu Gly Gln Gln Lys Lys
                565                 570                 575

Glu Leu Ala Ala Leu Leu Glu Ala Gln Lys Arg Thr Tyr Lys Leu Arg
            580                 585                 590

Lys Glu Gln Leu Lys Glu Glu Leu Gln Glu Asn Pro Ser Thr Pro Lys
            595                 600                 605

Arg Glu Lys Ala Glu Trp Leu Leu Arg Gln Lys Glu Gln Leu Gln Gln
            610                 615                 620

Cys Gln Ala Glu Glu Ala Gly Leu Leu Arg Arg Gln Arg Gln Tyr
625                 630                 635                 640

Phe Glu Leu Gln Cys Arg Gln Tyr Lys Arg Lys Met Leu Leu Ala Arg
                645                 650                 655

His Ser Leu Asp Gln Asp Leu Leu Arg Glu Asp Leu Asn Lys Lys Gln
                660                 665                 670

Thr Gln Lys Asp Leu Glu Cys Ala Leu Leu Leu Arg Gln His Glu Ala
            675                 680                 685

Thr Arg Glu Leu Glu Leu Arg Gln Leu Gln Ala Val Gln Arg Thr Arg
690                 695                 700

Ala Glu Leu Thr Arg Leu Gln His Gln Thr Glu Leu Gly Asn Gln Leu
705                 710                 715                 720

Glu Tyr Asn Lys Arg Arg Glu Gln Glu Leu Arg Gln Lys His Ala Ala
                725                 730                 735

Gln Val Arg Gln Gln Pro Lys Ser Leu Lys Val Arg Ala Gly Gln Leu
            740                 745                 750

Pro Met Gly Leu Pro Ala Thr Gly Ala Leu Gly Pro Leu Ser Thr Gly
            755                 760                 765

Thr Leu Ser Glu Glu Gln Pro Cys Ser Ser Gly Gln Glu Ala Ile Leu
770                 775                 780

Gly Gln Arg Met Leu Gly Glu Glu Glu Ala Val Pro Glu Arg Met
785                 790                 795                 800

Ile Leu Gly Lys Glu Gly Thr Thr Leu Glu Pro Glu Glu Gln Arg Ile
                805                 810                 815

Leu Gly Glu Glu Met Gly Thr Phe Ser Ser Pro Gln Lys His Arg
            820                 825                 830

Ser Leu Val Asn Glu Glu Asp Trp Asp Ile Ser Lys Glu Met Lys Glu
            835                 840                 845

Ser Arg Val Pro Ser Leu Ala Ser Gln Glu Arg Asn Ile Ile Gly Gln
            850                 855                 860

Glu Glu Ala Gly Ala Trp Asn Leu Trp Glu Lys Glu His Gly Asn Leu
865                 870                 875                 880

Val Asp Met Glu Phe Lys Leu Gly Trp Val Gln Gly Pro Val Leu Thr
                885                 890                 895

Pro Val Pro Glu Glu Glu Glu Glu Glu Glu Glu Gly Gly Ala Pro
            900                 905                 910
```

```
Ile Gly Thr Pro Arg Asp Pro Gly Asp Gly Cys Pro Ser Pro Asp Ile
        915                 920                 925

Pro Pro Glu Pro Pro Ser His Leu Arg Gln Tyr Pro Ala Ser Gln
        930                 935                 940

Leu Pro Gly Phe Leu Ser His Gly Leu Leu Thr Gly Leu Ser Phe Ala
945                 950                 955                 960

Val Gly Ser Ser Ser Gly Leu Leu Pro Leu Leu Leu Leu Leu Leu Leu
                965                 970                 975

Pro Leu Leu Ala Pro Arg Trp Arg Trp Leu Ala Gly Ser Thr Ala Gly
            980                 985                 990

Pro
```

(2) INFORMATION FOR SEQ ID NO: 5:

(i) SEQUENCE CHARACTERISTICS:
        (A) LENGTH: 414 base pairs
        (B) TYPE: nucleic acid
        (C) STRANDEDNESS: single
        (D) TOPOLOGY: linear (xi) SEQUENCE DESCRIPTION: SEQ ID NO: 5:

```
ACGANTCACC AGTTGGAAGT TACTCCAAAG AATGAGCACA AAACAATCTT AAAGACACTG    60

AAAGATGAGC AGACAAGAAA ACTTGCCATT TNGGCAGAGC AGTATGAACA GAGTATAAAT   120

GAAATGATGG CCTCTCANGC GTTACGGCTA GATGAGGCTC AAGAAGCAGA ATGCCAGGCC   180

TTGAGGCTAC AGCTCCAGCA GGAAATGGAG CTGCTCAACG CCTACCAGAG CAAAATCAAG   240

ATGCAAACAG AGGCACAACA TGAACGTGAG CTCCAGAAGC TAGAGCAGAG AGTGTCTCTG   300

CGCAGAGCAC ACCTTGAGCA GAAGATTGAA GAGGAGCTGG CTGCCCTTCA GAAGGAACGC   360

AGCGAGAGAA TAAAGAACCT ATTGGAAAGG CAAGAGCGAG AGATTGGAAA CTTT         414
```

(2) INFORMATION FOR SEQ ID NO: 6:

(i) SEQUENCE CHARACTERISTICS:
        (A) LENGTH: 314 base pairs
        (B) TYPE: nucleic acid
        (C) STRANDEDNESS: single
        (D) TOPOLOGY: linear (xi) SEQUENCE DESCRIPTION: SEQ ID NO: 6:

```
GAACAAAGTC ATGCCTTAAT AGTTCTGCTG ATGTTGGCCT TTCCTGAGGT ATTTTCTGCA    60

AGCAGTAATC AACAAATCTC CTAAAGGAGT CTGTCCATTC ATTAGACTGT AACGTTGGGG   120

AGTCATTCTG GGCAATGTGA TATAAGGCAC TCATTGCATT CATGTTGAAA AGGGGCGGCT   180

TCCGTTCCGC CAATTCAATA CAAGTGATGC CAAGTGACCA AATATCAACT TTCCCATCAT   240

ACTGTCCTTC ATCCATAGCT AAGATCACCT CTGGAGCCAT CCAGTAAGGT GTGCCCACGA   300

AGGAGTTGGC CAGG                                                     314
```

(2) INFORMATION FOR SEQ ID NO: 7:

(i) SEQUENCE CHARACTERISTICS:
        (A) LENGTH: 370 base pairs
        (B) TYPE: nucleic acid
        (C) STRANDEDNESS: single
        (D) TOPOLOGY: linear (xi) SEQUENCE DESCRIPTION: SEQ ID NO: 7:

```
ACCAAATTCC CAAATCCCAT TCTGAGGCTC TCCATGTCAA AAGTTTCAAT CTCTCGCTCT    60

TGCCTTTCCA ATAGGTTCTT TATTCTCTCG CTGCGTTCCT TCTGAAGGGC AGCCAGCTCC   120
```

```
TCTTCAATCT TCTGCTCAAG GTGTGGTCTG CGCAGAGACA CTCTCTGCTC TAGCTTCTGG      180

AGCTCACGTT CATGTTGTGC CTCTGTTNGN ATCTTGATTT GGNTCTGGTA GGCGTTGAGC      240

AGCTCCATTT CCTGCTGGAG CTGTAGCCTC AAGGCCTGGC ATTCTGCTTC TTGAGCCTCA      300

TCTAGCCGTA ACGCTTGAGA GGCCATCATT TCATTTATAC TCTGTTCATA CTGCTCTGCC      360

AAAATGGCAA                                                             370
```

(2) INFORMATION FOR SEQ ID NO: 8:

(i) SEQUENCE CHARACTERISTICS:
        (A) LENGTH: 190 base pairs
        (B) TYPE: nucleic acid
        (C) STRANDEDNESS: single
        (D) TOPOLOGY: linear (xi) SEQUENCE DESCRIPTION: SEQ ID NO: 8:

```
CAACAGCAGA AAAACTTAAA GGCCATGGAA ATGCAAATTA AAAAACAGTT TCAGGACACT       60

TGCAAAGTAC AGACCAAACA GTATAAAGCA CTCAAGAATC ACCAGTTGGA AGTTACTCCA      120

AAGAATGAGC ACAAAACAAT CTTAAAGACA CTGAAAGATG AGCAGACAAG AAAACTTGCC      180

ATTTTGGCAG                                                             190
```

(2) INFORMATION FOR SEQ ID NO: 9:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (xi) SEQUENCE DESCRIPTION: SEQ ID NO: 9:

```
GAGCAGTATG AACAGAGTAT AAATGAAATG ATGGCCTCTC AAGCGTTACG GCTAGATGAG       60

GCTCA                                                                   65
```

(2) INFORMATION FOR SEQ ID NO: 10:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (xi) SEQUENCE DESCRIPTION: SEQ ID NO: 10:

```
ACGAGTCCCC CCGAGAGCTA GAGTACAGGC AGCTGCACAC GTTACAGAAG CTACGCATGG       60

ATCTGATCCG TTTACAGCAC CAGACGGAAC TGGAAAACCA GCTGGAGTAC AATAAGAGGC      120

GAGAAAGAGA ACTGCACAGA AAGCATGTCA TGGAACTTCG GCAACAGCCA AAAAACTTAA      180

AGGCCATGGA ANTGCAATTT AAAAAACAGT TCCAGGAAA                             219
```

(2) INFORMATION FOR SEQ ID NO: 11:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO: 11:

```
GTGCATATGG TATATTTNAT TCATTTTTGT AAAGCGTTCT GTTTTGTGTT TACTAATTGG       60

GATGTCATAG TACTTGGCTG CCGGG                                             85
```

(2) INFORMATION FOR SEQ ID NO: 12:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO: 12:

```
CTCACTTGGG TACTACAGTG TGGAAGCTGA GTGCATATGG TATATT                  46
```

(2) INFORMATION FOR SEQ ID NO: 13:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (xi) SEQUENCE DESCRIPTION: SEQ ID NO: 13:

```
GATATTTGGT CATTGGGTAT CACGTGTATA GAGCTGGCCG AACGTCGTCC ACCATTGTTC   60

AGTATGAATG CAATGTCTGC CCTCTACCAT ATTGCTCAAA ATGATCCTCC AACTCT      116
```

(2) INFORMATION FOR SEQ ID NO: 14:

(i) SEQUENCE CHARACTERISTICS:
        (A) LENGTH: 118 base pairs
        (B) TYPE: nucleic acid
        (C) STRANDEDNESS: single
        (D) TOPOLOGY: linear (xi) SEQUENCE DESCRIPTION: SEQ ID NO: 14:

```
CTGAAAGGCC TGGATTATCT GCACTCAGAG CGCAAGATCC ACCGAGATAT CAAAGCTGCC   60

AACGTGCTGC TCTCGGAGCA GGGTGATGTG AAGATGGCAG ACTTCGGTGT GGCTGGCA   118
```

(2) INFORMATION FOR SEQ ID NO: 15:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (xi) SEQUENCE DESCRIPTION: SEQ ID NO: 15:

```
GACCCAGAGG AACTCTTCAC CAAGCTTGAC CGCATTGGCA AAGGCTCATT TGGGGAGGTG   60

TACAAGGGGA TCGACAACCA CACCAAGGAA GTGGTGGCCA TCAAGATCAT            110
```

(2) INFORMATION FOR SEQ ID NO: 16:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (xi) SEQUENCE DESCRIPTION: SEQ ID NO: 16:

```
TCAGGATTCT GGAGCTCTGG AGTTCCATTA GTGGCTATCA GATACAATGC CCTGAGTGGA   60

TTTTCATTAA GGTAAGGGGG TTCACCTTCC ACCATTTCAA TTGCCATAAT TCCAAGAGAC  120

CAGATATCAA CTTT                                                    134
```

(2) INFORMATION FOR SEQ ID NO: 17:

(i) SEQUENCE CHARACTERISTICS:

(A) LENGTH: 278 amino acids
        (B) TYPE: amino acid
        (C) STRANDEDNESS:
        (D) TOPOLOGY: linear (xi) SEQUENCE DESCRIPTION: SEQ ID NO: 17:

Met Ala Pro Ala Val Leu Gln Lys Pro Gly Val Ile Lys Asp Pro Ser
1               5                   10                  15

Ile Ala Ala Leu Phe Ser Asn Lys Asp Pro Glu Gln Asp Leu Arg Glu
            20                  25                  30

Ile Gly His Gly Ser Phe Gly Ala Val Tyr Phe Ala Tyr Asp Lys Lys
        35                  40                  45

Asn Glu Gln Thr Val Ala Ile Lys Lys Met Asn Phe Ser Gly Lys Gln
50                  55                  60

Ala Val Glu Lys Trp Asn Asp Ile Leu Lys Glu Val Ser Phe Leu Asn
65                  70                  75                  80

Thr Val His Pro His Ile Val Asp Tyr Lys Ala Cys Phe Leu Lys
                85                  90                  95

Asp Thr Thr Cys Trp Leu Val Met Glu Tyr Cys Ile Gly Ser Ala Ala
                100                 105                 110

Asp Ile Val Asp Val Leu Arg Lys Gly Met Arg Glu Val Glu Ile Ala
            115                 120                 125

Ala Ile Cys Ser Gln Thr Leu Asp Ala Leu Arg Tyr Leu His Ser Leu
        130                 135                 140

Lys Arg Ile His Arg Asp Ile Lys Ala Gly Asn Ile Leu Leu Ser Asp
145                 150                 155                 160

His Ala Ile Val Lys Leu Ala Asp Phe Gly Ser Ala Ser Leu Val Asp
                165                 170                 175

Pro Ala Gln Thr Phe Ile Gly Thr Pro Phe Phe Met Ala Pro Glu Val
            180                 185                 190

Ile Leu Ala Met Asp Glu Gly His Tyr Thr Asp Arg Ala Asp Ile Trp
        195                 200                 205

Ser Leu Gly Ile Thr Cys Ile Glu Leu Ala Glu Arg Arg Pro Pro Leu
210                 215                 220

Phe Ser Met Asn Ala Met Ser Ala Leu Tyr His Ile Ala Gln Asn Asp
225                 230                 235                 240

Pro Pro Thr Leu Ser Pro Ile Asp Thr Ser Glu Gln Pro Glu Trp Ser
                245                 250                 255

Leu Glu Phe Val Gln Phe Ile Asp Lys Cys Leu Arg Lys Pro Ala Glu
            260                 265                 270

Glu Arg Met Ser Ala Glu
            275

(2) INFORMATION FOR SEQ ID NO: 18:

(i) SEQUENCE CHARACTERISTICS:
        (A) LENGTH: 273 amino acids
        (B) TYPE: amino acid
        (C) STRANDEDNESS:
        (D) TOPOLOGY: linear (xi) SEQUENCE DESCRIPTION: SEQ ID NO: 18:

Arg Glu Glu Arg Glu Arg Arg Lys Lys Gln Leu Tyr Ala Lys Leu Asn
1               5                   10                  15

Glu Ile Cys Ser Asp Gly Asp Pro Ser Thr Lys Tyr Ala Asn Leu Val
            20                  25                  30

Lys Ile Gly Gln Gly Ala Ser Gly Gly Val Tyr Thr Ala Tyr Glu Ile

-continued

```
              35                  40                  45
Gly Thr Asn Val Ser Val Ala Ile Lys Gln Met Asn Leu Glu Lys Gln
     50                  55                  60

Pro Lys Lys Glu Leu Ile Ile Asn Glu Ile Leu Val Met Lys Gly Ser
 65                  70                  75                  80

Lys His Pro Asn Ile Val Asn Phe Ile Asp Ser Tyr Val Leu Lys Gly
                 85                  90                  95

Asp Leu Trp Val Ile Met Glu Tyr Met Glu Gly Ser Leu Thr Val
                100                 105                 110

Asp Val Val Thr His Cys Ile Leu Thr Gly Gln Ile Gly Ala Val
                115                 120                 125

Cys Arg Glu Thr Leu Ser Gly Leu Glu Phe Leu His Ser Lys Gly Val
130                 135                 140

Leu His Arg Asp Ile Lys Ser Asp Asn Ile Leu Leu Ser Met Glu Gly
145                 150                 155                 160

Asp Ile Lys Leu Thr Asp Phe Gly Phe Cys Ala Gln Ile Asn Glu Leu
                165                 170                 175

Asn Leu Lys Arg Thr Thr Met Val Gly Thr Pro Tyr Trp Met Ala Pro
            180                 185                 190

Glu Val Val Ser Arg Lys Glu Tyr Gly Pro Lys Val Asp Ile Trp Ser
            195                 200                 205

Leu Gly Ile Met Ile Ile Glu Met Ile Glu Gly Glu Pro Pro Tyr Leu
210                 215                 220

Asn Glu Thr Pro Leu Arg Ala Leu Tyr Leu Ile Ala Thr Asn Gly Thr
225                 230                 235                 240

Pro Lys Leu Lys Glu Pro Glu Asn Leu Ser Ser Ser Leu Lys Lys Phe
                245                 250                 255

Leu Asp Trp Cys Leu Cys Cys Val Glu Pro Glu Asp Arg Ala Ser Ala
            260                 265                 270

Thr
```

(2) INFORMATION FOR SEQ ID NO: 19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ix) FEATURE:
        (A) NAME/KEY: -
        (B) LOCATION: 24
        (D) OTHER INFORMATION: /note= "Where N is inosine"

(ix) FEATURE:
        (A) NAME/KEY: -
        (B) LOCATION: 31
        (D) OTHER INFORMATION: /note= "Where N is inosine"

(xi) SEQUENCE DESCRIPTION: SEQ ID NO: 19:

GACGCTGGAT CCAAAGATAC TGGNCAAGGG NGC                                    33

(2) INFORMATION FOR SEQ ID NO: 20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ix) FEATURE:

```
            (A) NAME/KEY: -
            (B) LOCATION: 3
            (D) OTHER INFORMATION: /note= "Where N is inosine"

(ix) FEATURE:
            (A) NAME/KEY: -
            (B) LOCATION: 6
            (D) OTHER INFORMATION: /note= "Where N is inosine"

(ix) FEATURE:
            (A) NAME/KEY: -
            (B) LOCATION: 13
            (D) OTHER INFORMATION: /note= "Where N is inosine"

(ix) FEATURE:
            (A) NAME/KEY: -
            (B) LOCATION: 16
            (D) OTHER INFORMATION: /note= "Where N is inosine"

(ix) FEATURE:
            (A) NAME/KEY: -
            (B) LOCATION: 19
            (D) OTHER INFORMATION: /note= "Where N is inosine"

(xi) SEQUENCE DESCRIPTION: SEQ ID NO: 20:

GGNGTNCCAG TTNGTNGCNA T                                               21

(2) INFORMATION FOR SEQ ID NO: 21:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ix) FEATURE:
            (A) NAME/KEY: -
            (B) LOCATION: 11
            (D) OTHER INFORMATION: /note= "Where N is inosine"

(ix) FEATURE:
            (A) NAME/KEY: -
            (B) LOCATION: 14
            (D) OTHER INFORMATION: /note= "Where N is inosine"

(ix) FEATURE:
            (A) NAME/KEY: -
            (B) LOCATION: 18
            (D) OTHER INFORMATION: /note= "Where N is inosine"

(xi) SEQUENCE DESCRIPTION: SEQ ID NO: 21:

AAAGGAAGCA NAGNCAGNAA CGGAAGAT                                        28

(2) INFORMATION FOR SEQ ID NO: 22:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ix) FEATURE:
            (A) NAME/KEY: -
            (B) LOCATION: 19
            (D) OTHER INFORMATION: /note= "Where N is inosine"

(ix) FEATURE:
            (A) NAME/KEY: -
            (B) LOCATION: 22
            (D) OTHER INFORMATION: /note= "Where N is inosine"

(xi) SEQUENCE DESCRIPTION: SEQ ID NO: 22:

GACGCTGAAT TCACCTTCNG GNGCCATCCA                                      30
```

-continued (2) INFORMATION FOR SEQ ID NO: 23:

(i) SEQUENCE CHARACTERISTICS:
        (A) LENGTH: 20 amino acids
        (B) TYPE: amino acid
        (C) STRANDEDNESS:
        (D) TOPOLOGY: linear (xi) SEQUENCE DESCRIPTION: SEQ ID NO: 23:

Thr Lys Asp Ala Val Arg Glu Leu Asp Asn Leu Gln Tyr Arg Lys Met
1               5                   10                  15

Lys Lys Leu Leu
            20

(2) INFORMATION FOR SEQ ID NO: 24:

(i) SEQUENCE CHARACTERISTICS:
        (A) LENGTH: 19 amino acids
        (B) TYPE: amino acid
        (C) STRANDEDNESS:
        (D) TOPOLOGY: linear (xi) SEQUENCE DESCRIPTION: SEQ ID NO: 24:

Lys Lys Glu Leu Asn Ser Phe Leu Glu Ser Gln Lys Arg Glu Tyr Lys
1               5                   10                  15

Leu Arg Lys (2) INFORMATION FOR SEQ ID NO: 25:

(i) SEQUENCE CHARACTERISTICS:
        (A) LENGTH: 20 amino acids
        (B) TYPE: amino acid
        (C) STRANDEDNESS:
        (D) TOPOLOGY: linear (xi) SEQUENCE DESCRIPTION: SEQ ID NO: 25:

Arg Glu Leu Arg Glu Leu Glu Gln Arg Val Ser Leu Arg Arg Ala Leu
1               5                   10                  15

Leu Glu Gln Lys
            20

(2) INFORMATION FOR SEQ ID NO: 26:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO: 26:

His Arg Asp Ile Lys Ala Gly Asn
1               5